US008895015B2

(12) United States Patent
Vesikari et al.

(10) Patent No.: US 8,895,015 B2
(45) Date of Patent: Nov. 25, 2014

(54) NOROVIRUS CAPSID AND ROTAVIRUS VP6 PROTEIN FOR USE AS COMBINED VACCINE

(75) Inventors: Timo Vesikari, Tampere (FI); Vesna Blazevic, Tampere (FI); Kirsi Nurminen, Tampere (FI); Leena Huhti, Tampere (FI); Suvi Lappalainen, Tampere (FI); Eeva Jokela, Tampere (FI)

(73) Assignees: Timo Vesikari, Tampere (FI); Vesna Blazevic, Tampere (FI)

( * ) Notice: Subject to any disclaimer, the term of this patent is extended or adjusted under 35 U.S.C. 154(b) by 233 days.

(21) Appl. No.: 13/269,326

(22) Filed: Oct. 7, 2011

(65) Prior Publication Data

US 2012/0093884 A1    Apr. 19, 2012

Related U.S. Application Data

(60) Provisional application No. 61/393,081, filed on Oct. 14, 2010.

(30) Foreign Application Priority Data

Oct. 15, 2010   (FI) ..................... 20106067

(51) Int. Cl.
*A61K 39/00*     (2006.01)
*A61K 39/12*     (2006.01)
*A61K 39/15*     (2006.01)
*A61K 39/125*    (2006.01)
*C12Q 1/70*      (2006.01)

(52) U.S. Cl.
CPC ..... *A61K 39/125* (2013.01); *C12N 2770/16034* (2013.01); *C12N 2720/12323* (2013.01); *A61K 39/15* (2013.01); *A61K 39/12* (2013.01); *C12N 2720/12334* (2013.01); *C12N 2770/16023* (2013.01); *C12N 2800/22* (2013.01); *C12N 2710/14143* (2013.01); *A61K 2039/70* (2013.01); *C12N 2799/026* (2013.01)
USPC ...... 424/184.1; 435/5; 424/204.1; 424/215.1; 424/216.1

(58) Field of Classification Search
CPC .......... C12N 2770/16022; C12N 2770/16023; C12N 2720/12323; C12N 2720/12334; A61K 2039/5258; A61K 39/12; A61K 39/00; A61K 39/125; A61K 2039/523; A61K 38/00; C07K 2319/00; C07K 14/005; C07K 2319/40
See application file for complete search history.

(56) References Cited

U.S. PATENT DOCUMENTS

| | | | |
|---|---|---|---|
| 6,673,355 B1 | 1/2004 | Estes et al. | |
| 7,527,801 B2 | 5/2009 | Coit et al. | |
| 2003/0166139 A1 | 9/2003 | Choi et al. | |
| 2007/0207526 A1* | 9/2007 | Coit et al. | 435/91.1 |
| 2008/0292660 A1 | 11/2008 | Kapikian et al. | |
| 2010/0322962 A1* | 12/2010 | Jiang et al. | 424/196.11 |

FOREIGN PATENT DOCUMENTS

WO    WO 2010/144602 A2    12/2010

OTHER PUBLICATIONS

Vesikari et al., Impact and Effectiveness of Rotateq® Vaccine Based on Three Years of Surveillance Following Introduction of a Rotavirus Immunization Program in Finland, 2013, The Pediatric Infectious Disease Journal, Publish Ahead of Print.*
Rocha-Pereira et al., The Viral Polymerase Inhibitor 2=-C-Methylcytidine Inhibits Norwalk Virus Replication and Protects against Norovirus-Induced Diarrhea and Mortality in a Mouse Model, 2013, Journal of Virology, vol. 87, No. 21, pp. 11798-11805.*
Charpilienne et al., Identification of Rotavirus VP6 Residues Located at the Interface with VP2 That Are Essential for Capsid Assembly and Transcriptase Activity, 2002, Journal of Virology, vol. 76, No. 15, pp. 7822-7831.*
Vesikari et al., "Efficacy of human rotavirus vaccine against rotavirus gastroenteritis during the first 2 years of life in European infants: randomised, double-blind controlled study," *The Lancet*, vol. 370, No. 9601, 2007, pp. 1757-1763.
Buesa et al., "Molecular Epidemiology of Caliciviruses Causing Outbreaks and Sporadic Cases of Acute Gastroenteritis in Spain," *Journal of Clinical Microbiology*, vol. 40, No. 8, 2002, pp. 2854-2859.
Burns et al., "Protective Effect of Rotavirus VP6-Specific IgA Monoclonal Antibodies That Lack Neutralizing Activity," *Science*, vol. 272, No. 5258, 1996, pp. 104-107.
Esquivel et al., "The internal rotavirus protein VP6 primes for an enhanced neutralizing antibody response," *Archives of Virology*, vol. 145, No. 4, 2000, pp. 813-825.
Estes, "Synthesis of Immunogenicity of the Rotavirus Major Capsid Antigen Using a Baculovirus Expression System," *Journal of Virology*, vol. 61, No. 5, 1987, pp. 1488-1494.
Fifis et al., "Size-Dependent Immunogenicity: Therapeutic and Protective Properties of Nano-Vaccines against Tumors," *The Journal of Immunology*, vol. 173, No. 5, 2004, pp. 3148-3154.
Huhti et al., "A comparison of methods for purification and concentration of norovirus GII-4 capsid virus-like particles," *Arch Virol*, vol. 155, 2010, pp. 1855-1858.
Jiang et al., "Expression, Self-Assembly, and Antigenicity of the Norwalk Virus Capsid Protein," *Journal of Virology*, vol. 66, No. 11, 1992, pp. 6527-6532.
Kanno et al., "Immunoglobulin G Antibody Avidity Assay for Serodiagnosis of Hepatitis C Virus Infection," *Journal of Medical Virology*, vol. 68, No. 2, 2002, pp. 229-233.
Keller et al., "Cutting Edge: Limited Specialization of Dendritic Cell Subsets for MHC Class II-Associated Presentation of Viral Particles," *The Journal of Immunology*, vol. 184, No. 1, 2010, pp. 26-29.
Lepault et al., "Structural polymorphism of the major capsid protein of rotavirus," *The EMBO Journal*, vol. 20, No. 7, 2001, pp. 1498-1507.
Makidon et al., "Pre-Clinical Evaluation of a Novel Nanoemulsion-Based Hepatitis B Mucosal Vaccine," *PloS ONE*, vol. 3, No. 8, 2008, pp. 1-15.
Matthijnssens et al., "Full Genomic Analysis of Human Rotavirus Strain B4106 and Lapine Rotavirus Strain 30/96 Provides Evidence for Interspecies Transmission," *Journal of Virology*, vol. 80, No. 8, 2006, pp. 3801-3810.

(Continued)

*Primary Examiner* — Benjamin P Blumel
(74) *Attorney, Agent, or Firm* — Oliff PLC

(57) ABSTRACT

The present invention relates to a combined norovirus and rotavirus vaccine for prevention of norovirus and rotavirus infection and/or viral-induced diarrheal and vomiting diseases in man. More specifically, the invention comprises a method of preparing combination vaccine compositions comprising norovirus and rotavirus antigens, in particular mixtures of norovirus VLPs and rotavirus recombinant VP6 protein or double-layered VP2/VP6 VLPs. In addition, the invention relates to methods of inducing an immune response.

13 Claims, 16 Drawing Sheets

(56) References Cited

OTHER PUBLICATIONS

Nurminen et al., "Prevalence of Norovirus GII-4 Antibodies in Finnish Children," *Journal of Medical Virology*, vol. 83, 2011, pp. 525-531.

Parez et al., "The VP6 Protein of Rotavirus Interacts with a Large Fraction of Human Naïve B Cells via Surface Immunoglobulins," *Journal of Virology*, vol. 78, No. 22, 2004, pp. 12489-12496.

Peralta et al., "Chimeric recombinant rotavirus-like particles as a vehicle for the display of heterologous epitopes," *Virology Journal*, vol. 6, No. 192, 2009, pp. 1-9.

Vesikari et al., "Safety and Efficacy of a Pentavalent Human-Bovine (WC3) Reassortant Rotavirus Vaccine," *The New England Journal of Medicine*, vol. 354, No. 1, 2006, pp. 23-33.

Bertolotti-Ciarlet et al., "Immunogenicity and protective efficacy of rotavirus 2/6-virus-like particles produced by a dual baculovirus expression vector and administered intramuscularly, intranasally, or orally to mice," *Vaccine*, 2003, pp. 3885-3900, vol. 21, No. 25-26, Elsevier Science Ltd.

Lobue et al., "Alphavirus-Adjuvanted Norovirus-Like Particle Vaccines: Heterologous, Humoral, and Mucosal Immune Responses Protect against Murine Norovirus Challenge," *Journal of Virology*, Apr. 2009, pp. 3212-3227, vol. 83, No. 7, American Society for Microbiology.

Zeng et al., "Norovirus gastroenteritis in young children receiving human rotavirus vaccine," *Scandinavian Journal of Infectious Diseases*, 2010, pp. 540-544, vol. 42, No. 6-7, Informa UK Ltd.

Blazevic et al., "Norovirus VLPs and rotavirus VP6 protein as combined vaccine for childhood gastroenteritis," *Vaccine*, 2011, pp. 8126-8133, vol. 29, No. 45, Elsevier Ltd.

Jan. 30, 2012 International Search Report issued in corresponding International Patent Application No. PCT/FI2011/050880.

\* cited by examiner

NOROVIRUS CAPSID AND ROTAVIRUS VP6 PROTEIN FOR USE AS COMBINED VACCINE

FIELD OF THE INVENTION

The present invention relates to vaccine formulations for preventing gastroenteritis especially in young children. More specifically, the present invention relates to combination vaccine formulations comprising at least one norovirus antigen and at least one rotavirus antigen.

BACKGROUND OF THE INVENTION

Rotavirus gastroenteritis causes more than 500 000 deaths every year in young children worldwide. Rotaviruses (RV), members of the family of Reoviridae, is the single most important causative agent of severe diarrhea in young children also in developed countries, resulting in fewer deaths than in developing countries but numerous hospitalizations at high cost. Live oral rotavirus vaccines have been available since 2006. Both the WHO and many indivictual countries now recommend vaccination of all healthy children against rotavirus.

In the development of a live oral rotavirus vaccine, Professor Timo Vesikari of the University of Tampere has played a key role. The first clinical trials of any rotavirus vaccine were conducted in Tampere in 1982. Prof. Vesikari and his team were instrumental in the pivotal trials establishing the efficacy and safety of the two currently licensed live oral rotavirus vaccines, the bovine-human reassortant pentavalent vaccine RotaTeq® (Merck) and the human rotavirus vaccine Rotarix® (GSK) (Vesikari et al. Safety and efficacy of a pentavalent human-bovine (WC3) reassortant rotavirus vaccine. N Engl J Med 2006;354:23-33; Vesikari et al. Efficacy of human rotavirus vaccine against rotavirus gastroenteritis during the first 2 years of life in European infants: randomised, double-blind controlled study. Lancet 2007;370:1757-63).

The currently available live attenuated oral rotavirus vaccines, while efficacious and successfully implemented in many countries, have potential safety issues that may limit their use in the long run. An earlier live oral rotavirus vaccine, based on rhesus rotavirus (RotaShield®, Wyeth), was withdrawn in the USA in 1999 because of association with intestinal intussusception, which may have occurred in about 1 in 10 000 recipients of the first dose of the vaccine. The currently licensed rotavirus vaccine does not involve such a great risk but a rare association cannot be excluded.

Furthermore, in 2010, it was discovered that both licensed live rotavirus vaccines contained porcine circovirus (PCV) DNA. Although the significance of this finding is unknown, it caused temporary suspension of one of the vaccines and a decrease in rotavirus vaccination overall. Both of these issues are inherent to live vaccines only, and together emphasize the need to develop non-live alternatives for rotavirus vaccines.

A rotavirus genome consists of 11 segments of double stranded RNA held in the inner core of the three-layered virus. The three layers consist of a core protein VP2 bound to dsRNA, an inner capsid protein VP6, and an outer capsid glycoprotein VP7 with hemagglutinin spike protein VP4. The major capsid protein VP6 determines viral group specificity and is the most conserved, immunogenic, and abundant rotavirus protein. The outer capsid proteins VP7 and VP4 contain neutralizing epitopes and induce protective immunity on the basis of neutralizing antibodies.

The mechanism of active protection induced by live oral rotavirus vaccines is not fully known. Surface proteins VP7 and VP4 are known to induce serotype specific neutralizing antibodies. However, there is significant cross-protection between serotypes that cannot be explained by serotype-specific immunity. VP6 is an immunodominant protein in rotavirus infection and after vaccination. Although VP6 does not induce neutralizing antibodies it induces heterologous rotavirus specific immunity.

The first rotavirus recombinant VP6 (rVP6) protein was produced from the rBV expression system more than two decades ago (Estes M et al. 1987). VP6 alone forms oligomeric structures including tubules, spheres and sheets in vitro composed of a variable number of trimers (Lepaualt J, Embo J, 20, 2001). Co-expression of VP2 and VP6 in rBVs results in the formation of double-layered virus-like particles (dl VLPs). Coexpression of VP2, VP6, and VP7 (with or without VP4) leads to triple-layered VLPs resembling native infectious rotavirus particles. A majority of the immunogenicity and vaccine efficacy studies in animal models has accomplished using different rotavirus VLPs or non-human recombinant VP6 protein with an adjuvant. No human clinical trials with the non-live subunit rotavirus protein vaccines using either VLPs or the recombinant VP6 protein have been accomplished so far.

After elimination or reduction of rotavirus in many areas, the relative role of norovirus as a causative agent is increasing. Noroviruses (NV) are members of the family Caliciviridae causing sporadic acute nonbacterial gastroenteritis in humans of all age groups, and are associated with outbreaks of gastroenteritis worldwide. NV cause annually approximately 1 million hospitalizations and more than 200 000 deaths worldwide in children less than 5 years of age. After rotavirus, the second most important viral cause of acute gastroenteritis in young children is norovirus.

A norovirus genome consists of a single stranded RNA of about 7.6 kb that is organized into three open reading frames (ORF 1-3). The ORF1 codes for RNA-dependent RNA polymerase similarly to other ssRNA viruses; the ORF2 encodes the major capsid protein VP1 and the ORF3 codes a small structural protein VP2. Most NVs affecting humans belong to two genogroups (GI and GII), and these two genogroups are divided into at least 8 GI and 17 GII genotypes. In recent years, it is the genotype GII-4 that has been primarily responsible for the majority of sporadic gastroenteritis cases and outbreaks.

A unique feature of the capsid VP1 protein is its ability to self-assemble into the empty virus-like particles (VLPs). Cloning of genogroup I Norwalk virus capsid gene into a recombinant baculovirus (rBV) has led to the production of the first norovirus VLPs twenty years ago (Jiang et al. 1992). These VLPs are morphologically and antigenically similar to the native NV. The three-dimensional structure of norovirus VLPs, viewed by using electron cryomicroscopy and computer image processing techniques, shows that the norovirus capsid forms a T=3 icosahedral symmetrical structure containing 180 molecules of the VP1 capsid proteins organized into 90 dimers with a diameter of 38 nm. Norovirus VLPs are widely used as a source of antigen in diagnostic serological assays, as well as for development of candidate vaccines against noroviruses. Although the receptor/s for norovirus binding and entry is/are not completely elucidated, it has recently been found that NV recognize human histo-blood group antigens (HBGAs) as receptors. Among the HBGAs, the most commonly encountered blood groups are ABO (ABH) and Lewis. These complex carbohydrates are found on the red blood cells and mucosal epithelial cells or as free antigens in biological fluids. Further, it has recently been found that the recognition of HBGAs by NV is strain-specific, and several distinct receptor binding patterns have been identified.

For norovirus, a live vaccine is not an option, because noroviruses cannot be cultivated in a cell culture. Therefore, the candidate vaccines for norovirus have been and are likely to be either VLP vaccines or soluble antigen vaccines.

The use of non-replicating subunit vaccines and subviral particles in modern vaccine design started in the mid 80's with the discovery of Hepatitis B surface antigen (HBsAg) particles found in blood of HB infected patients. These vaccines are generally safe as they are deprived of any live attenuated or inactivated viruses or their genetic material, and they are relatively easily and cost effectively produced in high quantities. An example of a subunit protein vaccine are virus like particles (VLPs) which mimic empty shells of live viruses and therefore possess antigenic and immunogenic properties similar to those of the live virus. Vaccine induced serum neutralizing antibodies are important to for protection against viral infections. Essential features of VLPs include that they resemble the natural virus and therefore retain neutralizing epitopes which are conformation-dependent.

There are several intriguing features or major attributes of NV VLPs and RV VP6 protein which make them promising vaccine candidates. Because of their repetitive, multivalent structures, VLPs are extremely immunogenic. The presentation of an antigen in a highly organized, dense, repetitive array on the surface of VLPs provokes strong antibody responses at very low doses, whereas the same antigen presented as a monomer is normally nonimmunogenic. B cells are efficiently activated by these repetitive structures (as are VLPs or rVP6 trimers organized into hexagons and packed into the higher order structures, e.g. tubules) which lead to cross-linking of B cell receptors on the cell surface. The particulate nature of VLPs, especially in a size range of around 40 nm, which is optimal for uptake of nanoparticles by professional antigen presenting cells (APC), namely dendritic cells (DC), via macropinocytosis and endocytosis (Fifis T., J Immunol, 2004, 173). Therefore, VLPs similarly to live viruses directly activate and mature DC without the need for other cells. DC play a central role in activating innate and adaptive immune responses and are involved in long lived memory IgG production and are the only APC capable of activating naïve T cells. VLPs efficiently prime CTL in the absence of intracellular replication (Keller S A et al., Intro, J Immunol, 2010). Therefore, VLPs are efficient in stimulating both cell mediated immunity (CMI) and humoral immune response.

As already mentioned above, VP6 is the most abundant and immunogenic subgroup-specific antigen of rotavirus. The ability of VP6 to form multimeric structures and the strong immune response that VP6 can elicit make it an excellent rotavirus vaccine candidate. VP6 does not induce neutralization antibodies to rotavirus but instead induces heterotypic cross-protective immunity by eliciting strong T helper (Th) cell responses which promote cross-reactive immunity (Burns J W et al., 1996 Science; Parez N et al, 2004, J Virol). VP6-specific CD4+ Th cells provide cognate help to B cells specific for neutralizing epitopes on the VP7 and/or VP4 molecules (Esquirel F R, Arch. Virol 2000, 145, 813). In addition, VP6-specific CD4+ Th cells were shown to protect against murine rotavirus infection either by a direct cytotoxic mechanism in mucosa or by antiviral cytokines production.

Given the severity of rotavirus and norovirus infections and deficiencies in the currently available vaccines, there is a need for both non-live norovirus and rotavirus vaccines, especially for the prevention of acute gastroenteritis in childhood.

Immune responses to NV and RV are complex, and the correlates of protection are not completely elucidated. Collectively, the above-described unique properties attributed to the VLPs including NV VLPs and to the VP6 protein of RV suggest that a vaccine consisting of these two components represents a viable strategy to immunize against NV and RV infection.

BRIEF DESCRIPTION OF THE INVENTION

The present invention is based on the surprising finding that norovirus and rotavirus antigens comprised in a combination vaccine do not interfere with each other but elicit a synergistic immunity against each of the antigens present in the vaccine.

The present invention thus provides a vaccine composition comprising at least one norovirus VLP antigen and at least one rotavirus VP6 antigen.

In some embodiments, the vaccine composition further comprises a norovirus antigen selected from a group consisting of antigenic capsid peptides, and antigenic capsid proteins. The antigen may be derived from any norovirus strain, such as those belonging to GI and GII genogroups and any genotypes thereof. In some embodiments, the norovirus antigen is GII-4 VLP, preferably in a monovalent form. In some other embodiments, the norovirus antigen comprises more than one VLP type.

In some embodiments, the rotavirus VP6 antigen is selected from a group consisting of rVP6 protein, double-layered VP2/VP6 VLP and VLPs comprising VP6 protein. The rVP6 may be in the multimeric form of tubules, spheres or sheets.

The present invention further provides a use of the described vaccines for preventing gastroenteritis, especially in young children. This aspect of the invention may also be formulated as a method of preventing gastroenteritis in a subject in need thereof, especially a young child, comprising vaccinating the subject with a vaccine composition described herein.

Furthermore, the present invention provides a method of producing vaccine compositions described herein. The method comprises i) co-expressing at least one norovirus and at least one rotavirus antigen in a single host, or ii) the steps of a) producing, isolating, and purifying at least one norovirus antigen; b) producing, isolating, and purifying at least one rotavirus antigen; and c) mixing said norovirus and rotavirus antigens. Preferably, the antigens are produced in a recombinant baculovirus-infected insect cell host.

Other objects, aspects, details, and advantages of the present invention will become apparent from the following drawings, detailed description, and examples.

BRIEF DESCRIPTION OF THE FIGURES

In the following, the invention will be described in greater detail by means of preferred embodiments with reference to the attached figures, in which.

Figure 12:
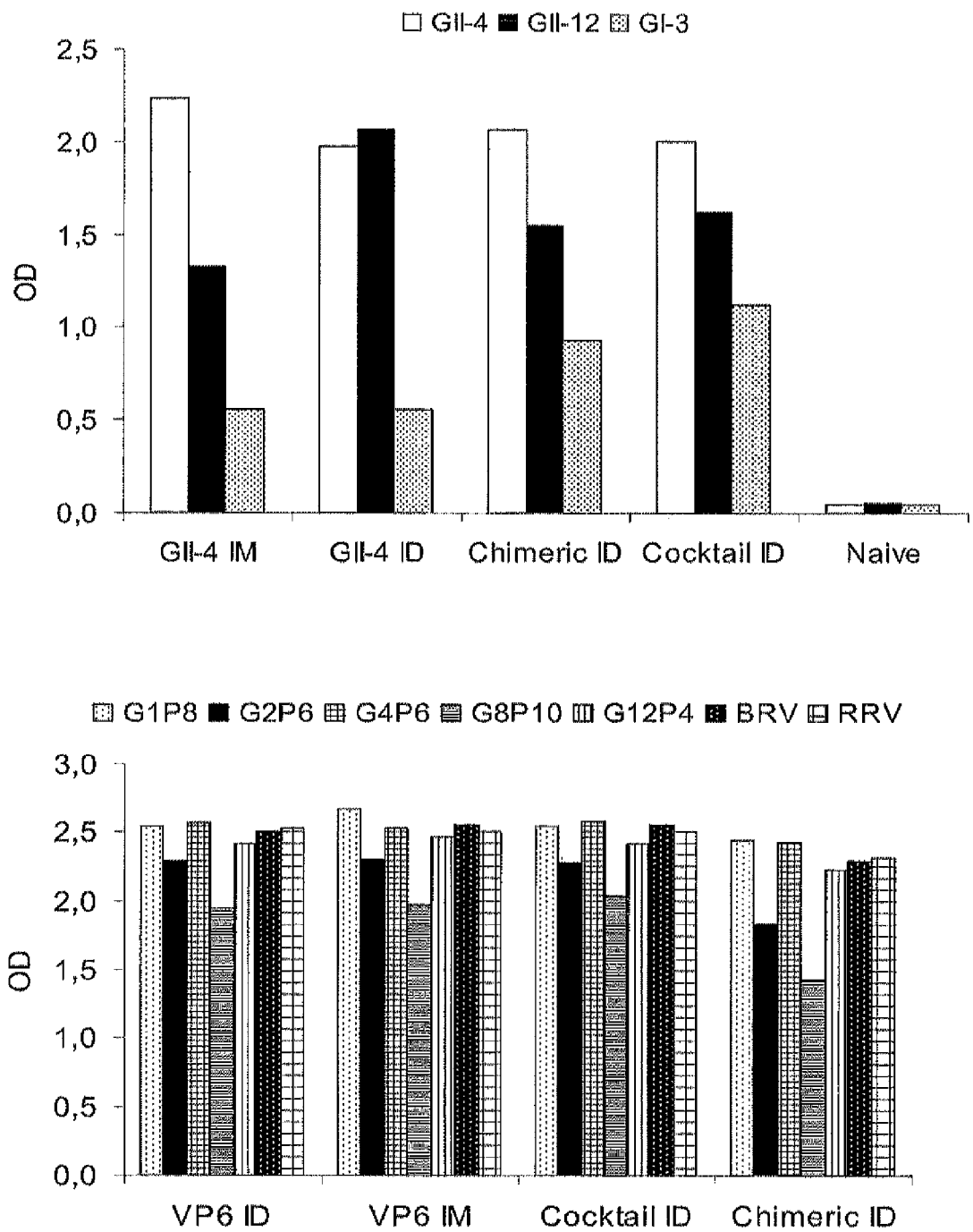

The upper panel in FIG. 12 represents the cross-reactivity of GII-4 VLP-induced IgG antibodies towards different NV genotypes (GII-12 and GI-3). The lower panel illustrates the cross-reactivity of rVP6 induced antibodies towards several human (G1P8, G2P6, G4P6, G8P10, and G12P4), bovine (BRV) and rhesus (RRV) rotavirus strains as measured in ELISA.

Figure 13:
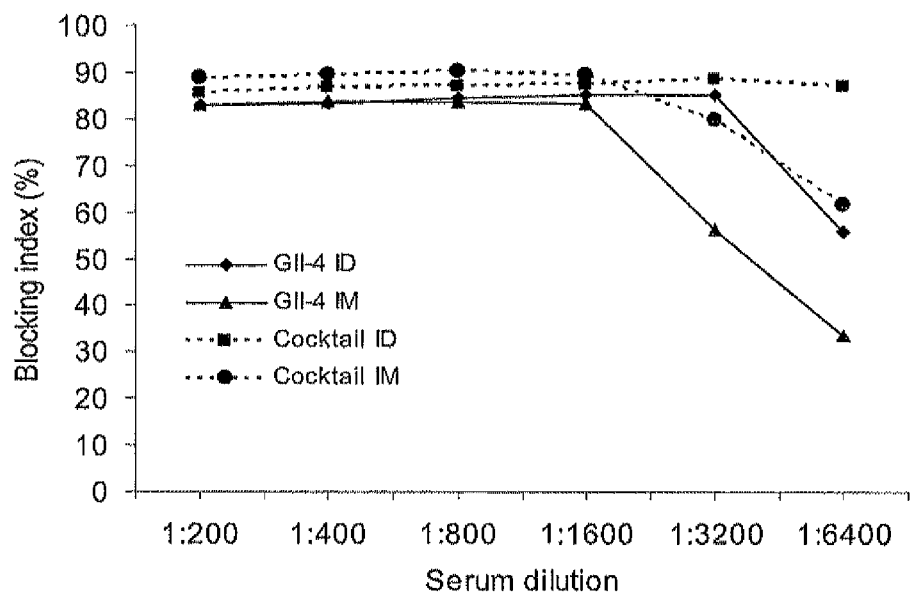
Figure 13:
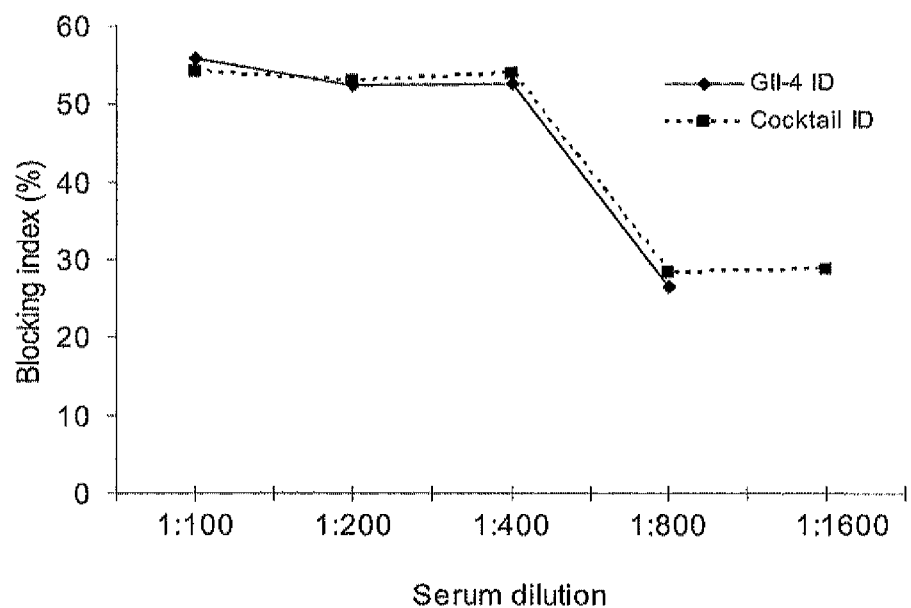
Figure 13:
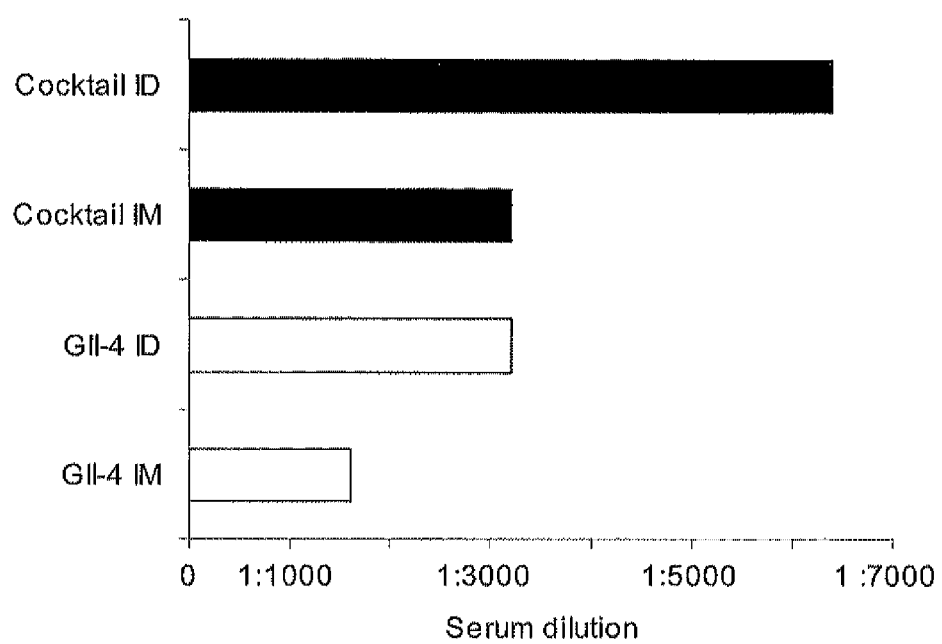

FIG. 13 illustrates the ability of NV GII-4-specific serum antibodies to block the binding of the homologous GII-4 VLPs (panel A) or the heterologous GI-3 VLPs (panel B) to the human histo-blood group antigen (HBGA) H-type-3 (a putative NV GII-4 receptor). Panel C shows the end point titer of the sera needed to maximally block the binding of GII-4 VLPs to H-type 3. The blocking index was calculated as follows: 100%—(OD[with serum]/OD[without serum]× 100%).

Figure 14:
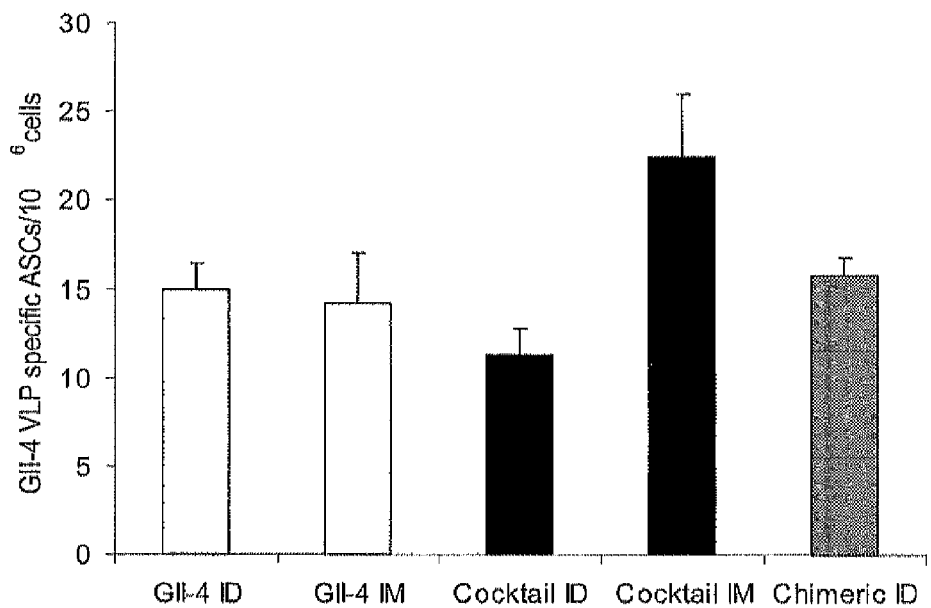
Figure 14:
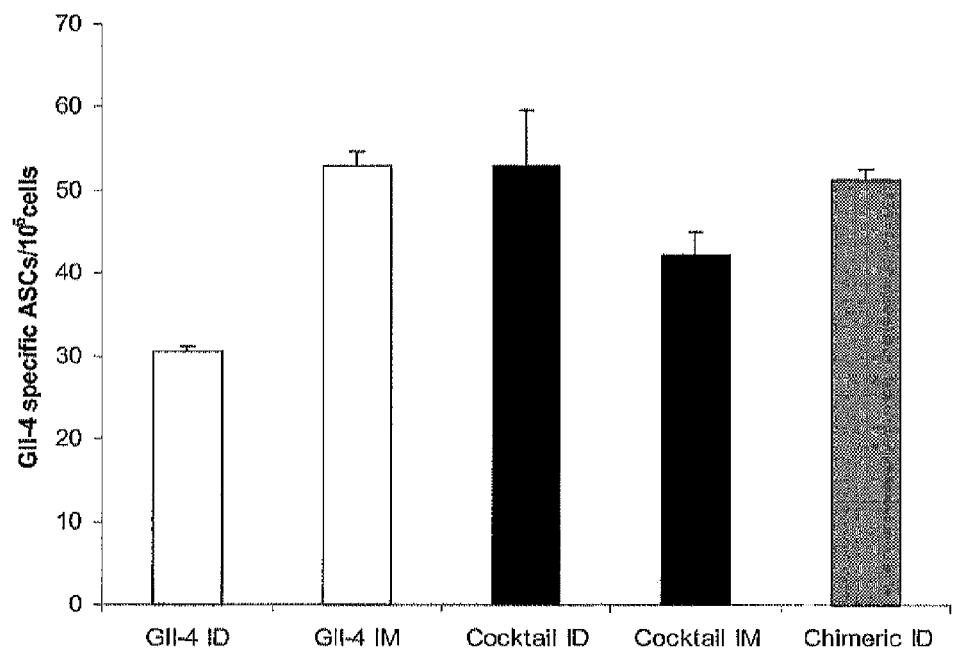

FIG. 14 shows the ELISPOT assay results of splenocytes harvested from mice immunized with different vaccine formulations. The upper panel illustrates GII-4 VLP-specific IgG antibody secreting cells (ASCs) at the day of harvesting the cells while the lower panel shows the number of GII-4 VLP-specific ASCs after 4 days in culture with GII-4 VLPs. The difference in the number of ASCs between the upper and the lower panels indicates the memory B cell response.

DETAILED DESCRIPTION OF THE INVENTION

The present invention relates to combination vaccine formulations comprising at least one norovirus (NV) antigen and at least one rotavirus (RV) antigen.

It has been surprisingly found out that norovirus and rotavirus antigens do not block the immunogenicity of each other, as is the case in many other combination vaccines. In the present vaccines, there is no interference between the individual antigens in the combination, such that the combined vaccine of the present invention is able to elicit immunity against each of the antigens present in the vaccine. Suitably, the immune response against a single component in the combination is at least 50% of the immune response of that component when measured individually, preferably 100% or substantially 100%. The immune response may suitably be measured, for example, by antibody responses, as illustrated in the examples herein. The present vaccine formulations not only lack negative interference between the individual antigens but also provide a synergistic effect.

Norovirus antigens suitable for use in the present invention include, but are not limited to, antigenic capsid proteins, peptides, monomers, dimers, VLPs, or any combination thereof. The norovirus antigens may be derived from a norovirus belonging to either GI or GII genogroup and having a desired genotype. In some embodiments, the norovirus antigen is selected from a group consisting of GII-4, GII-12, and GI-3 VLPs. Because genotype GII-4 is a major cause of acute norovirus gastroenteritis worldwide, a preferred norovirus antigen for use in the present vaccines is GII-4 VLPs. Preferably, the VLPs are monovalent.

Rotavirus VP6 is a subgroup-specific antigen which is the most abundant and immunogenic rotavirus protein inducing cross-reactive antirotavirus responses. Rotavirus-specific serum antibodies of mice immunized with the present vaccine formulations were cross-reactive towards different human, bovine and simian rotavirus strains belonging to the subgroups 1 and 2, as is the case with a majority of rotavirus serotypes infecting human beings (FIG. 12).

Rotavirus VP6, recombinant VP6 (rVP6) in multimeric or in any other form, or any rotavirus VLP comprising the VP6 may be used as a rotavirus antigen in the present vaccine formulations. Co-expression of VP2 and VP6 in recombinant baculoviruses results in the formation of double-layered virus-like particles (dl VP2/VP6 VLPs). Such VLPs are included as suitable rotavirus antigens for use in the present vaccine formulations. Rotavirus antigens may be derived from any rotavirus strain but are preferably human from human rotavirus.

The norovirus and rotavirus antigens described above may be used in any desired combination in the present vaccine formulations. In some embodiments, the vaccine formulation comprises monovalent GII-4 norovirus VLPs and rotavirus rVP6 protein, preferably in multimeric form. In some other embodiments, the vaccine formulation comprises monovalent GII-4 norovirus VLPs and rotavirus double-layered VP2/VP6 VLPs.

Norovirus and rotavirus antigens may be isolated and purified from natural sources. In other embodiments, said antigens may be produced by recombinant techniques in suitable expression systems, including but not limited to, yeast cells (e.g. *S. cerevisiae, S. pombe* or *Pichia pastori*), bacterial cells (e.g. *E. coli*), insect cells (e.g. Sf9 cells), and mammalian cells (e.g. CHO cells). Suitable expression vectors for each expression system are well known to a person skilled in the art.

The present vaccines may comprise a combination of single norovirus and rotavirus vaccines at any ratio, preferably in equal quantities (1:1). A combination vaccine may be formulated at least in two ways. In a first way, where norovirus and rotavirus vaccines are produced as recombinant proteins separately (either in the form of VLPs, monomers, dimers, trimers, spheres, tubules, sheets or any combination thereof) and mixed in vitro at a certain ratio to obtain a liquid formulation referred to as a "cocktail" vaccine. In a second way, chimeric proteins of norovirus capsid and rotavirus VP6 are obtained by co-infecting a desired host (e.g. Sf9 insect cells) with a suitable expression system (e.g. recombinant baculoviruses expressing a norovirus capsid gene and a rotavirus VP6 gene). Such vaccine formulations are herein referred to as "chimeric" vaccines.

In addition to a type-specific (homotypic) immune response, induction of a cross-reactive (heterotypic) immune response is of high significance when viruses like norovirus and rotavirus are in question. These viruses have large numbers of different genotype/serotypes and strains circulating. An ideal vaccine induces a response to variable strains homologous and heterologous to the virus found in the vaccine. In some embodiments, GI-3 (belonging to the norovirus genogroup I) and GII-12 (belonging to the norovirus genogroup II) VLPs were identified as heterologous antigens to GII-4 VLPs present in the vaccine formulations. Mice immunized with a GII-4 specific single or combination vaccine generated antibodies reactive to both of the heterologous antigens, across the genogroup and therebetween. The approximately 50% increase in the cross-reactive immune response towards GI-3 in the sera of mice immunized with the combination vaccine compared to a rotavirus VP6 single vaccine indicates an adjuvant effect of the rotavirus VP6 protein present in the vaccine formulation. In other words, the antigenic components of the present combination vaccines provide a synergistic effect. In the examples, it is demonstrated that the RV VP6 protein has the ability to act as an adjuvant in terms of broadening the immune response induced by the vaccine antigen and increasing the blocking activity of the sera.

In addition to the cross-reactive responses, the present combination vaccine formulations induce strong, systemic, long lasting (memory), and blocking IgG antibody responses and cell-mediated immunities specific to noroviruses and rotaviruses by any immunization route (preferably ID and IM routes). These responses are in contrast to the short-lived and type-specific natural response generated after an infection. Thus, a systemic immune response in contrast to the local mucosal response might be necessary for a longer duration of protection.

Transfer of serum IgG antibodies into the gut lumen is likely to provide an important mechanism of protection against gut infection. It can be anticipated that the higher the systemic immune response elicited by a parenterally (ID/IM) administered vaccine as the one described herein, the higher the level of transferred antibodies and the better the protection.

Furthermore, the present vaccine formulations induce a mixed balanced type of the immune response, namely T helper (Th) cell type 1 and Th2 type responses. This is an important observation considering that both types of the immune response are likely to mediate protection against the infection with norovirus and/or rotavirus.

In addition, the present vaccine formulations are potent inducers of the high avidity antibodies, as demonstrated in the Examples. High avidity antibodies were shown to significantly correlate with the protective efficacy of the vaccines.

Moreover, the invention shows that cross-protection between genogroups is achievable with the vaccine formulations used herein. Immunization with VLPs from a certain strain/genotype of norovirus, as the GII-4 VLP described herein (a so-called monovalent vaccine), will not only induce a cross-reactive or heterotypic immune response against other genotypes not included in the vaccine formulations (GI-3 and GII-12 used herein) but it will also block heterologous virus binding and neutralize the virus as described herein.

In addition to the active ingredients, i.e. norovirus and rotavirus antigens, that elicit immune stimulation, the present formulations may comprise sterile, nontoxic, pharmaceutically acceptable physiological carriers. In some embodiments, the vaccine formulation may further comprise preservatives such as phenol, 2-phenoxyethanol or thimerosal, to prevent bacterial or fungal contamination, and/or stabilizers such sucrose, lactose, amino acids, or gelatin to stabilize the vaccine against adverse conditions and to prevent the immunogens from adhering to the wall of the vial.

In some embodiments, the present vaccine formulations may comprise an effective amount of one or more adjuvants. One of the main features of the adjuvant substances in general is to broaden the immune response induced by the vaccine antigens. The term "effective amount of adjuvant" includes an amount of adjuvant which is capable of stimulating the immune response against an administered antigen, i.e. an amount that increases the immune response of an administered antigen composition, as measured for example in terms of cross-reactivity and blocking antibody activity in the sera as illustrated in the examples herein. Suitable effective increases include those by more than 5%, preferably by more than 25%, and in particular by more than 50%, as compared to the same antigen composition with no adjuvant. Adjuvants suitable for use in vaccine formulations are known to a person skilled in the art.

The present vaccine formulations may be provided in various forms including, but not limited to, aqueous solutions and dry powders (lyophilized formulations). For example, aqueous solutions may be provided in a form suitable to be administered by injection, nasal delivery (e.g. as sprays or nasal drops), and oral delivery.

The vaccine formulations may be administered by various routes, as is readily understood by a person skilled in the art. Preferably, the vaccine formulations of the present invention are administered via parenteral injections including, but not limited to, intramuscular (IM), intradermal (ID) or subcutaneous (SC) injections.

Various administration regimes may be applied to the present vaccine formulations. Since severe acute rotavirus gastroenteritis and norovirus gastroenteritis have a similar peak incidence between 6 months and 3 years of age, a combined norovirus and rotavirus vaccine could be targeted at children in this age bracket in the following two non-limiting ways:

a) An injectable norovirus+rotavirus vaccine could be part of a routine immunization schedule of young infants. It is believed that 2 doses of the vaccine would be sufficient for infants, possibly followed by a booster dose later. In Finland, the routine immunization schedule is at 3, 5, and 12 months of age. The present norovirus+rotavirus vaccine would fit into such a schedule. While other countries have somewhat different schedules, the proposed vaccine could easily be adopted in different programs, to be given at 2, 4, and 12 months, 4, 6, and 12 months and so on;

b) An injectable norovirus rotavirus vaccine could be used as a booster vaccination for rotavirus and primary vaccination for norovirus at 12 to 15 months of age. Two doses would be given. This option might be used if live oral rotavirus vaccines continue to be used for primary immunization against rotavirus at the ages of 2 to 6 months. It is known that immunity against rotavirus will wane in the second and third year of life, and a booster vaccination would be desirable in many cases. However, live oral vaccines cannot be used for booster vaccination because of the greater risk for intussusception at an older age, i.e. the time of normal booster vaccinations.

An injectable norovirus rotavirus vaccine given in 2 doses between the ages of 12 and 15 months would serve as a booster vaccination for rotavirus and as a primary vaccination for norovirus. While a (small) proportion of norovirus gastroenteritis is in infants less than 12 months of age, the majority of the cases occur after this age and the vaccine would still have the potential to prevent most of the cases of norovirus gastroenteritis in young children.

The present vaccines may be used in preventing or lessening norovirus and rotavirus infection, norovirus- and rotavirus-induced diarrheal and vomiting diseases as well as gastroenteritis, and in inducing an immune response against norovirus and rotavirus in a subject in need thereof by vaccinating the subject with a pharmaceutically effective amount of the present vaccine formulation. A "pharmaceutically effective amount" of the vaccine is an amount which is able to elicit an immune response that protects the vaccine recipient against norovirus and rotavirus.

EXAMPLES

It will be obvious to a person skilled in the art that, as technology advances, the inventive concept can be implemented in various ways. The invention and its embodiments are not limited to the examples described below but may vary within the scope of the claims.

Example 1

Norovirus VLPs Production and Purification

Extraction and Cloning of Norovirus GII-4 Capsid Gene

Norovirus GII-4 was isolated from patient stool in 1999 in Finland. RNA from the stool was extracted with a QiaAmp RNA viral mini kit (Qiagen, Germany). A DNA fragment containing the complete gene of norovirus VP1 capsid gene (1620 bp) was amplified by the reverse transcriptase polymerase chain reaction (RT-PCR) with the following primers: JV24 forward (5'-GTGAATGAAGATGGCGTCGA-3'; SEQ ID NO:1) (Buena et al., 2002) and reverse (5'-TTATAATG-CACGTCTACGCCC-3'; SEQ ID NO:2). The full length DNA copy of VP1 capsid sequence was obtained by sequencing with an ABI PRISM™ 310 Genetic analyzer (Applied Biosystems, USA). The norovirus strain in question was classified into genetic cluster according to EMBL/Genbank and the European Food-borne Viruses in network (FBVE) (GenBank sequence database accession number AF080551). The complete VP1 capsid gene was amplified with the following primers: GII-4-fwd (5'CACAGGATCCATGAAGATG-GCGTCGAATGAC-3'; SEQ ID NO:3) and GII-4-rev (5'CICTGAATTCTTATAATGCACGTC-TACGCCCCGCTCCA-3'; SEQ ID NO:4) using the PTC-200 DNA Engine (MJ Research). The amplified fragment was cloned into pCR2.1-TOPO vector (Invitrogen, USA) and further subcloned into the baculovirus pFastBac1 transfer vector (Invitrogen). After transformation into TOP10 chemically competent E. coli cells the VP1 was verified by sequencing with an ABI PRISM™ 310 Genetic Analyzer (Applied Biosystems).

Extraction and Cloning of Norovirus GII-12 and GI-3 Capsid Genes

Stool specimens were collected from norovirus infected patients in Finland. RNAs were extracted (Qiagen) as described above. The norovirus GII-12 VP1 capsid gene and GI-3 VP1 capsid gene were amplified by the RT-PCR with the following primers:

```
GII-12-fwd
(5'-GTGAATGAAGATGGCGTCGA-3'; SEQ ID NO: 5),

GII-12 rev
(5'TTACTGTACTCTTCTGCGCCC-3'; SEQ ID NO: 6)
and

GI-3 fwd
(5'-GTAAATGATGATGGCGTCTAA-3'; SEQ ID NO: 7)
and

GI-3 rev
(5'-TGGGCCATTATGATCTCCTAAT-3'; SEQ ID NO: 8).
```

The amplicons (1.6 Kb) were sequenced and strains were classified according to EMBL/Genbank and FBVE (GenBank sequence database accession number GII-12 AJ277618 and GI-3 AF414403). Norovirus VP1 capsid genes (GII-12 and GI-3) were codon-optimized. GII-12 was cloned into the pFastBacDual transfer vector (Invitrogen) and GI-3 was cloned into the pFastBac1 transfer vectors (Invitrogen).

Norovirus Capsid Recombinant Baculovirus (BV) Stocks Production

To generate a recombinant bacmid, a pFastBac construct was transformed into DH10Bac™ competent E. coli by a Bac-to-Bac Baculovirus expression system (Invitrogen) according to the manufacturer's instructions. Bacmid DNA was purified from 2 ml overnight LB culture by PureLink HiPure Plasmid DNA Miniprep Kit (Invitrogen). Recombinant bacmid DNA was analyzed by PCR to verify the presence of gene in the bacmid. For analyzing pUC/M13, forward and reverse primers (Invitrogen) were used. VLPs were produced in Spodoptera frugiperda (Sf9) insect cells infected with the recombinant baculovirus according to the Bac-to-Bac expression system. To be more precise, Sf9 cells were seeded in Multidish 6-wells (Nunc, Thermo Fisher, Denmark) at $1 \times 10^6$ cells/ml of serum free medium (Sf 900 SFM III; Invitrogen) and transfected by bacmid DNA (1 µg) using Cellfectin (Invitrogen). The cells were grown at 26° C. and harvested 72 hours post-transfection. Cell suspension was centrifuged at 500×g for 5 min and the supernatant (P1 baculovirus stock) was aliquoted and stored at 4° C. Sf9 cells were infected with the baculoviral P1 stock and after six days post-infection (dpi) the cell suspension was centrifuged at 500×g for 5 min and aliquoted supernatant (P2 baculovirus stock) was stored at 4° C. Baculovirus titers (plaque forming units; pfu) expressed as the multiplicity of infection (MOI) of the P2 stocks were determined by the BacPak Rapid Titer kit (Clontech laboratories, USA).

Recombinant (r) Norovirus Capsid Expression and VLP Production and Purification

For the production of the norovirus VLPs, 200 ml Sf9 cell cultures were set up at a density of $1 \times 10^6$ cells/ml and cells were infected with P2 stock at MOI of 1. At day six, infected cell culture was clarified by centrifugation at 3000×g for 30 min at 4° C. VLPs in the supernatant were concentrated by ultracentrifugation (L8-60M ultracentrifuge, Beckman SW-32.1 Ti rotor) at 100,000×g for 2 hours at 4° C. and pellets were resuspended in 3 ml 0.2 M Tris-HCl (pH 7.3). VLPs were loaded onto a 10% to 60% discontinuous sucrose gradient and ultracentrifugated at 100,000×g for 1 h at 4° C. Fractions were collected by bottom puncture. Approximately 25 fractions were collected and each fraction was analyzed by SDS-PAGE for the expression of capsid proteins. Analysis of indicated fractions of the first sucrose gradient fractions showed that an apparent peak of the capsid protein migrated to 35% sucrose, and these fractions were pooled. Further, the GII-4 VLPs were purified with an additional discontinuous sucrose gradient (35% to 60%). Fractions containing VLPs were collected and pooled. Sucrose was removed by overnight dialysis against 1 l of phosphate-buffered saline (PBS). VLPs were concentrated by ultrafiltration. Briefly, up to 15 ml of dialyzed product was concentrated using an Amicon Ultra 30 kDa centrifuge filter device (Millipore Corporation, Germany) according to the manufacturer's instructions. VLPs were stored at 4° C. in PBS. Total protein concentration was quantified by using a Pierce® BCA Protein Assay (Thermo Scientific, USA). Purity and integrity was verified by 12% SDS-PAGE followed by a densitometric analysis and EM.

Example 2

Rotavirus Antigens

A. Rotavirus rVP6 Production and Purification
Extraction and Cloning of Rotavirus VP6
To obtain the complete nucleotide sequence of a VP6 gene segment, RNA of 10% stool suspension originating from a strong G1[P8] RT-PCR positive acute gastroenteritis patient was extracted by a QIAamp RNA viral mini kit (Qiagen) according to the manufacturer's instructions. Extracted dsRNA was subjected to RT-PCR reactions with a specific primer pair of VP6 (Matthijnssens et al., 2006) producing amplicon of 1362 bp. The amplicon was purified by a QIAquick gel extraction kit (Qiagen) and sequenced by an ABI PRISM TM 310 Genetic Analyzer (Applied Biosystems). The sequence of VP6 amplicon was codon-optimized and cloned into a pFastBac1 vector (Invitrogen).
Rotavirus VP6 Recombinant Baculovirus (BV) Stock Production
The production was performed essentially as described above in connection with norovirus.
Rotavirus rVP6 Production and Purification
For the production of recombinant VP6, 200 ml of Sf9 insect cells was infected with the recombinant baculoviruses containing the gene of VP6 at an MOI of 5 pfu/cell at a cell concentration of 1×10$^6$ cell/ml. Culture supernatants were collected at 6 dpi and clarified at 1000 rpm for 20 min at +4° C. A recombinant protein was concentrated by ultracentrifugation at 100 000×g for 1.5 h at +4° C. and pellets were resuspended in 0.2 M Tris-HCl (pH 7.3), and purified on continuous sucrose gradients (10% to 60%) at 100 000×g for 16 h at +4° C. Additional sucrose gradient purification might be applied as well. Fractions of a sucrose containing VP6 protein were pooled, dialysed overnight against PBS and concentrated by centrifugation in Amicon Ultra-50 centrifugal filter units (Millipore Corporation). Proteins were stored at 4° C. in PBS. Total protein concentration was quantified using a Pierce® BCA Protein Assay. Purity and integrity were verified by 12% SDS-PAGE followed by a densitometric analysis and EM.

B. Double-Layered (dl) Rotavirus VP2/VP6 VLPs Production and Purification
Extraction and Cloning of Rotavirus VP2
To obtain the complete nucleotide sequence of a VP2 gene segment, RNA of the same G1[P8] RT-PCR positive acute gastroenteritis patient was extracted by a QIAamp RNA viral mini kit (Qiagen) as described in connection with the rotavirus rVP6 production and purification. RT-PCR reaction was performed with a specific primer pair of VP2 (Matthijnssens et al., 2006) to produce amplicon of 2662 bp. The amplicon was purified and sequenced in a manner similar to that used in connection with VP6. The sequence of VP2 amplicon was codon-optimized and cloned into pFastBacDual vector (Invitrogen).
Rotavirus VP2 Recombinant Baculovirus (BV) Stock Production
The production was performed essentially as described above in connection with norovirus.
Rotavirus dl VP2/VP6 VLPs Production and Purification
In order to produce rotavirus double-layered (dl) VP2/VP6 VLPs, Sf-9 insect cells were co-infected with the recombinant BVs containing the genes of VP2 and VP6 at equal MOI/cell, at a cell concentration of 1×10$^6$ cell/ml. Culture supernatants were collected at 7 dpi and clarified at 1000 rpm for 20 min at +4° C. Recombinant VP2/6-VLPs were concentrated and purified on continuous sucrose gradients similarly to the recombinant norovirus Fractions of sucrose containing VP2 and VP6 were pooled, dialysed against PBS and concentrated by centrifugation in Amicon Ultra-100 centrifungal filter units (Millipore Corporation). VLPs were stored at 4° C. in PBS. Total protein was quantified using a Pierce® BCA Protein Assay (Thermo Scientific). Purity and integrity of the VP2/6 were verified by 12% SDS-PAGE and EM. The proportion of VP6 in VP2/VP6 sample was quantified by a densitometric analysis.

Example 3

Chimeric Protein (GII-4 Capsid+VP6) Production and Purification

Chimeric protein preparations were produced by co-infecting Sf9 insect cells with norovirus GII-4 rBV at MOI of 5 and rotavirus VP6 rBV at MOI of 5. Supernatants of co-infected insect cells were harvested at 6 dpi. The cell culture was clarified by centrifugation at 3000×g for 30 min at 4° C. and the supernatant was ultracentrifugated 100 000×g for 2 hours at 4° C. The pellets were resuspended in 0.2 M Tris-HCl (pH 7.3) and the chimeric proteins were co-purified by a continuous sucrose gradient (10% to 60%) at 100 000×g for 3 hours at 4° C. Fractions containing both recombinant proteins (NV capsid and RV VP6, respectively) were collected by bottom puncture and analyzed by SDS-PAGE. The fractions from 40% sucrose containing the chimeric protein were pooled and sucrose was removed by dialysis against PBS. The dialyzed product was concentrated with an Amicon Ultra 30 kDa centrifuge filter device. Products were stored at 4° C. in PBS. The total protein concentration was quantified using a Pierce® BCA Protein Assay (Thermo Scientific). Purity and integrity of each protein were verified by 12% SDS-PAGE followed by a densitometric analysis and EM.

Example 4

Characterization of Norovirus and Rotavirus VLPs

SDS-PAGE and Densitometric Quantitation

Samples were run in SDS-PAGE (sodium dodecyl sulfate polyacrylamide gel electrophoresis) using polyacrylamide gels with 12% acrylamide in the separating gel and 5% in the stacking gel (Biorad Laboratories, USA). Samples were boiled for 5 min in Laemmli sample buffer containing 2% SDS, 5% β-mercaptoethanol, 62. mM Tris-HCl (pH 6.8), 25% glycerol, and 0.01% Bromophenol Blue (Biorad). Gels were stained with PageBlue™ Protein Staining Solution (Fermentas, Lithuania).

Proteins run on SDS-PAGE gel were quantitated by AlphaEase® FC Software (Alpha Innotech, USA) according to the manufacturer's instructions.

Figure 1:
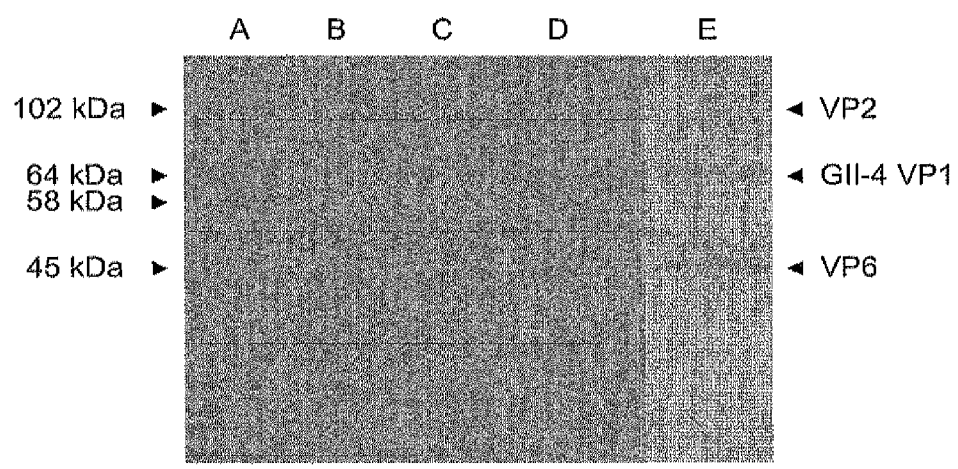
FIG. 1A is a photograph of a page blue stained 12% SDS-PAGE gel demonstrating the purity of baculovirus expressed norovirus GII-4 VLPs (lane A), rotavirus rVP6 (lane B), double-layer VP2/VP6 VLPs (lane C), cocktail vaccine (norovirus GII VLPs rVP6; lane D), and chimeric vaccine (co-infected norovirus GII-4 capsid and rotavirus VP6; lane E). Different proteins are indicated by arrowheads to the right of the gel. Corresponding molecular weights (kDa) of the each protein are indicated to the left of the gel.
FIG. 1B shows electron micrographs of the morphological structures assembled by the recombinant proteins. The proteins were purified and the structures were examined by electron microscopy, followed by staining with 3% uranyl acetate. VLP structures were detected for norovirus (NV) GII-4 capsid, and rotavirus (RV) VP2/VP6 (panels A and C) and tubular structures were observed for VP6 protein (panel B). Both GII-4 VLPs and tubules of VP6 were observed in panel D (cocktail vaccine formulation) and panel E (chimeric vaccine formulation).

FIG. 1A shows photographs of the page blue stained gels with the identified proteins of expected molecular weight marked with an arrowhead. Chimeric proteins of GII-4 capsid and rotavirus VP6 were detected in the same fractions of the sucrose gradient. FIG. 1A shows purified proteins on the SDS-PAGE.

Electron Microscopy (EM)

The preparations were negatively-stained with 3% uranyl acetate (UA) (pH 4.6). 3 µl of the protein sample was applied to a carbon coated grid for 30 sec. The grid was dried and 3 µl of UA was applied to the grid for further 30 sec. Excess liquid was removed and the grid was examined by a FEI Tecnai F12 electron microscope (Philips Electron Optics, Holland) operating at 120 kV.

Figure 1B:
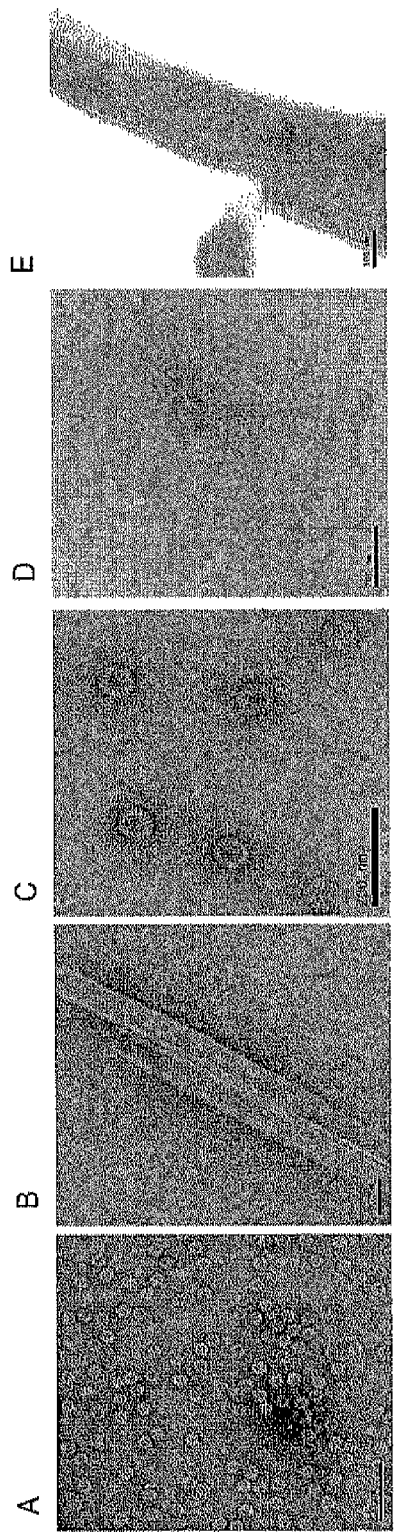

Each protein was examined for morphology under EM (FIG. 1B) and high order structures including GII-4 VLPs, rVP6 tubules, and dl VP2/VP6 VLPs were confirmed. Tubules of rVP6 are shown but any forms of rVP6 protein can be assembled including, but not limited to, trimers and higher order multimeric structures including spheres and sheets. Mixing of the GII-4 VLPs and rVP6 into a cocktail at a ratio of 1:1 did not impair protein integrity or the morphology of either part in the cocktail. Similar morphological features were detected for the cocktail vaccine and the chimeric vaccine, identifying rVP6 tubules filled with the GII-4 VLPs. Other structures of the NV capsid and RV VP6 can also be formed.

Example 5

Mice Immunizations

Female BALB/c mice 7 to 9 weeks old (4 to 5 mice/group) were immunized intradermally (ID) or intramuscularly (IM) with different vaccines two times, at week 0 and week 3. In some instances, mice received only one immunization with the vaccine. Vaccines used for immunization were as follows: GII-4 VLPs, rVP6 protein, dl VP2/VP6 VLPs, cocktail (a mix of GII-4 VLPs and rVP6), chimeric vaccine, and cocktail VLP (a mix of GII-4 VLPs and dl VP2/VP6 VLPs). The vaccine doses used were: 50 µg, 10 µg, 1 µg and 0.1 µg. In most instances, mice were immunized with 10 µg of a single vaccine formulation or 20 µg of the combination vaccine (cocktail or chimeric). 10 µg of each single vaccine component is contained in the cocktail vaccine. For example, to obtain the cocktail vaccine, 10 µg of the GII-4 VLPs in PBS was mixed with 10 µg of rVP6 in PBS in vitro and stored at +4° C. Blood (serum) samples and faeces were collected at weeks 0 (pre-bleed, non-immune sera), 2, 3, and 4. The mice were euthanized 2 weeks after the final immunization and faeces, whole blood, and lymphoid tissue were collected. Naïve mice receiving no vaccine formulation were used as controls.

Example 6

Figure 2:
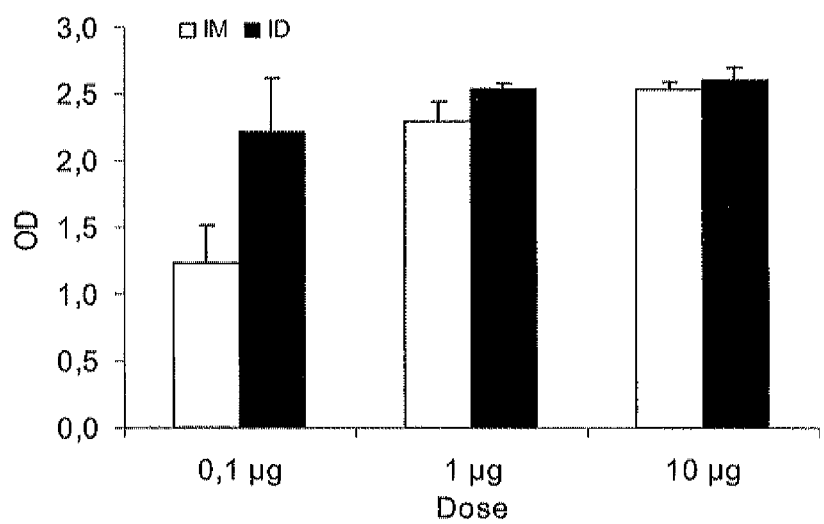
FIG. 2 illustrates the result of an ELISA assay of a norovirus (NV)-specific IgG response after immunizations of BALB/c mice with different doses and routes (intramuscular, IM and intradermal, ID) of GII-4 VLPs.
Figure 3:
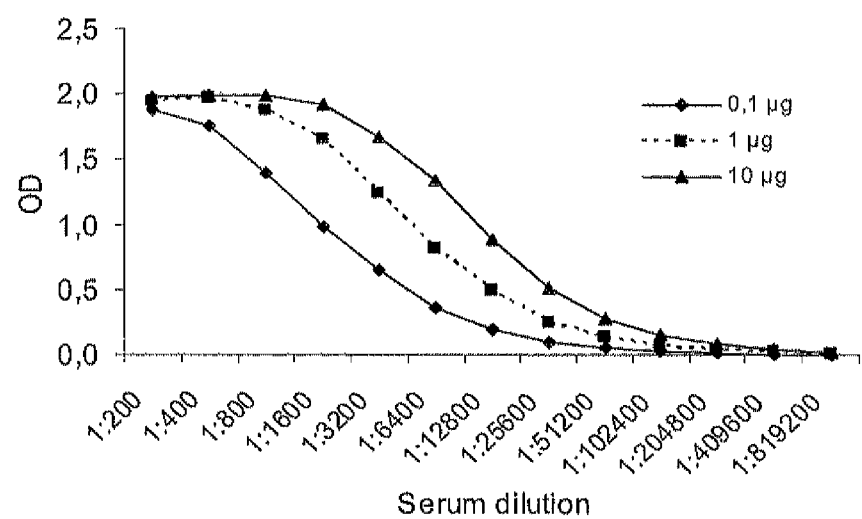
FIG. 3 illustrates the result of an NV-specific IgG serum end point titration assay after immunizations with different doses of GII-4 VLPs via ID route.
Figure 4:
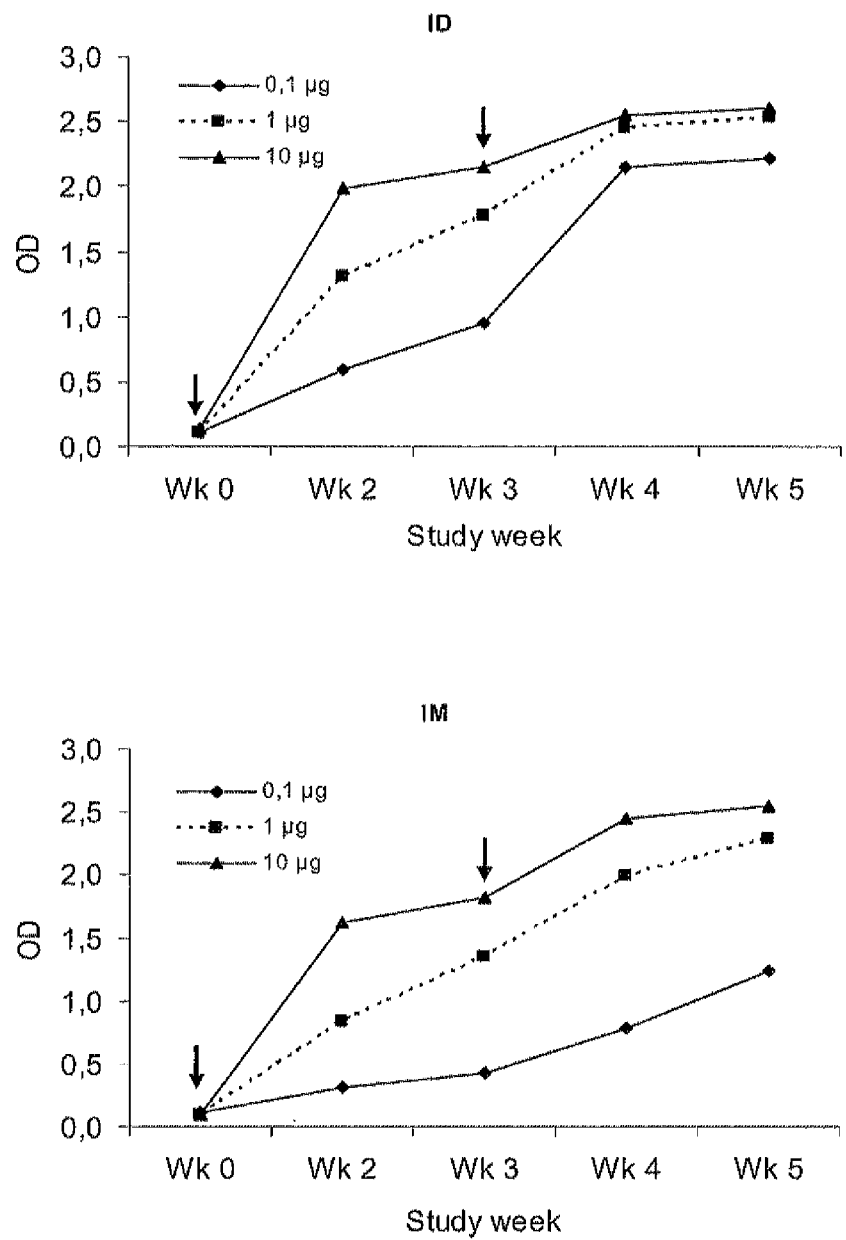
FIG. 4 shows kinetics of NV-specific IgG immune response development in sera of mice immunized with different doses of GII-4 VLPs and measured in an ELISA. The upper panel shows the result of ID immunization and the lower panel that of IM immunization.
Figure 5:
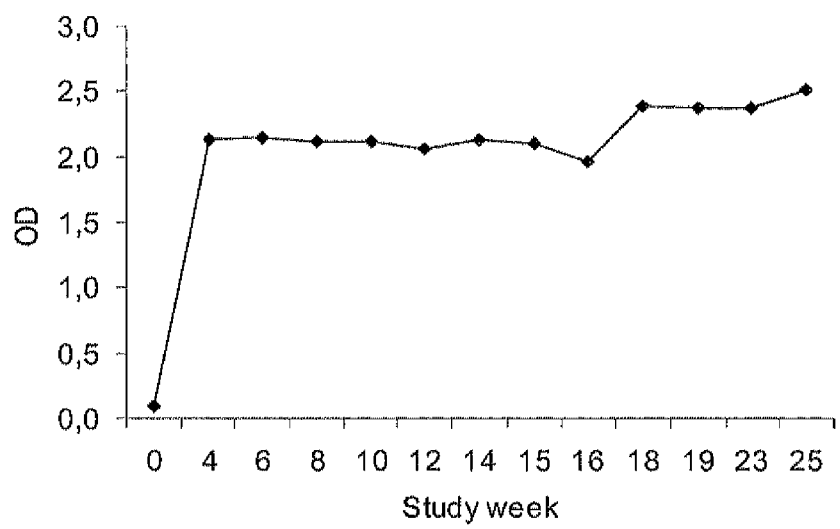
FIG. 5 illustrates duration of an NV-specific IgG response after IM immunizations with GII-4 VLPs tested in an ELISA.

Dose Response, Kinetics, and Duration of the Immune Response Induced by the Vaccine Groups of mice (5 mice/group) were immunized with 10, 1 or 0.1 µg of GII-4 VLPs at day 0 and 21 by IM and ID routes. Serum was collected at week 0, 2, 3, and 4 and the mice were terminated at week 5. Each termination serum was tested at 1:200 dilution for NV-specific IgG. There was a similar level of the response induced by the 10 and 1 µg doses but a somewhat lower response was observed with the 0.1 µg dose (FIG. 2). In addition, the end point titer of pooled sera from the above groups of mice was similar (FIG. 3). Control naïve mice had no responses to NV. FIG. 4 shows the kinetics of the immune response measured in weekly collected sera. Immunization points are shown by an arrow. The results show that immunization with one dose induces a very potent immune response, especially for the 10 µg and 1 µg doses. A 50 µg dose induced a similar response to the 10 µg dose, determining the plateau of the response at the 10 µg dose. Altogether, these results identify 10 and 1 µg doses as the optimal ones although other doses of vaccine formulations can be used. In addition, a 10 µg dose induced a long lasting immune response which did not fade till week 25 (FIG. 5).

Example 7

Faecal Analysis

Transfer of the IgG from the sera into the gut lumen has been associated with the protection against enteric pathogens like NV and RV. The ability of IgG in the intestine to mediate protection against RV infection or ameliorate disease has been shown by passive immunoglobulin treatments in children.

To test the effect of single vaccine formulations or combination vaccines on the possible transfer of IgG, fresh mice faeces were suspended in 10 mM Tris buffer containing 100mM NaCl, 1 mM $CaCl_2$, 0.05% Tween, 1% aprotinin and 10 µM leupeptine (all from Sigma-Aldrich) to resume 10% faecal suspension which was homogenized by vortexing. Homogenized suspensions were kept on ice for 20 minutes and centrifuged for 15 minutes 18 000×g at +4° C. The supernatants were extracted and stored at −80° C.

Faecal samples were tested for norovirus GII-4 and rotavirus VP6 specific IgG in ELISA as described for serum antibody ELISA with some modifications. After coating and blocking, faecal samples (10% faecal suspension) were 2-fold serially diluted from 1:2 to 1:32 and added to the plate. Goat anti-mouse IgG-HRP (Sigma-Aldrich) was diluted 1:3000 and the plate was developed and the absorbance measured as described above.

Figure 8:
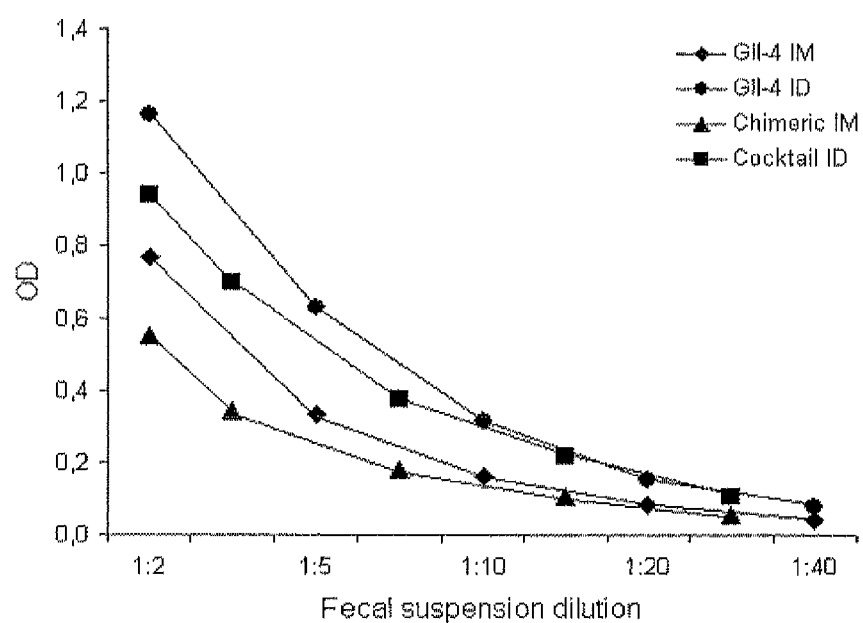
FIG. 8 illustrates the results of an NV-specific faecal IgG end point titration assay after immunizations of mice with GII-4 VLPs alone or in the cocktail or the chimeric formulation with rVP6.

FIG. 8 shows that a significant level of NV-specific IgG in the faeces of immunized mice but not in that of the control mice was detected.

Example 8

Serum Analyses

Groups of mice were immunized as described above with each single vaccine formulation or the combination vaccine. IgG subtypes IgG1 and IgG2a were measured from the sera of immunized mice to be able to determine the type of the immune response induced by the vaccine formulations. The relationship between the T helper (Th) 1 and Th2 dichotomy and predominant immunoglobulin isotype has been determined: IgG1 is classified as the Th2-type response and IgG2a as the Th1-type response. The Th1-type is promoting cell mediated immunity and the Th2-type humoral immunity.

Norovirus Serum IgG and IgG Subtype ELISA

Sera from immunized and control mice were tested for immunoglobulin G (IgG), IgG1 and IgG2a by an enzyme linked immunosorbent assay (ELISA). Norovirus GII-4, GII-12, and GI-3 VLPs were used to coat (4° C., overnight) 96-well microtiter plates (Nunc Immuno Maxisorp, Thermo Fisher Scientific Inc., Waltham, Mass., USA) in 10 mM PBS at concentrations of 0.2 µg/ml, 0.4 µg/ml and 1 µg/ml (100 µl/well), respectively. After washing three times with PBS containing 0.05% Tween 20 (PBS-T), the plates were blocked at room temperature (RT) for 1 h with PBS containing 5% skimmed milk (Sigma-Aldrich). The wells were then washed three times with PBS-T and incubated 1 h at 37° C. with 100 µl of serum diluted 1:200 or two-fold dilution series in PBS-T containing 1% skimmed milk. All serum samples were tested in duplicate wells. After washing six times, horseradish peroxidase (HRP) conjugated anti-mouse IgG (Sigma-Aldrich) diluted 1:4000 in 1% milk in PBS-T was added to the wells. Anti-GII-4 IgG subtype responses were determined using a goat anti-mouse IgG1 or IgG2a HRP conjugate (Invitrogen, Carlsbad, Calif.) diluted 1:6000 in 1% milk in PBS-T. After incubation (1 h, 37° C.), the plates were washed and o-phenylenediamine dihydrochloride (SIGMAFAST OPD, Sigma-Aldrich) substrate was added at a concentration of 0.4 mg/ml. The plates were incubated at RT in the dark for 30 minutes and the reaction was stopped with 2 M sulphuric acid ($H_2SO_4$). Absorbance (optical density, OD) at a wavelength of 490 nm was measured in a microplate reader (Victor2 1420, Perkin Elmer, Waltham, Mass., USA). One known positive and one negative serum sample from a naïve mouse was added to all plates as controls. A background signal from the blank wells (wells without serum) was subtracted from all of the OD readings at a plate. A sample was considered positive if the net absorbance value was above the set cut-off value, calculated as follows: mean OD (naïve mice)+3×SD and at least 0.100 OD.

Rotavirus Serum IgG and IgG Subtype ELISA

VP6 protein was used to coat 96-well microtiter plates in Bicarbonate/Carbonate buffer (0.1 mM $Na_2CO_3$, 0.8 mM $NaHCO_3$, pH 9.55) at a concentration of 1 µg/ml (100 µl/well). After the above step, ELISA was performed similar to ELISA for norovirus. For detection of cross-reactive rota-specific serum antibodies, Polyclonal Rabbit Anti-Rotavirus (Human) (DAKO) was diluted 1:200 with Bicarbonate/Carbonate buffer and used 100 µl/well for coating microtiter plates (+4° C. overnight). After washing four times with PBS-T, the plates were coated with 100 µl/well of rotavirus antigen (4° C. overnight) prepared as described above. After washing four times with PBS-T the plates were blocked at +37° C. for 1 h with PBS containing 5% skimmed milk. After this step ELISA was performed similarly to serum ELISA for norovirus.

Serum IgG Magnitude and Subtypes

Figure 6:
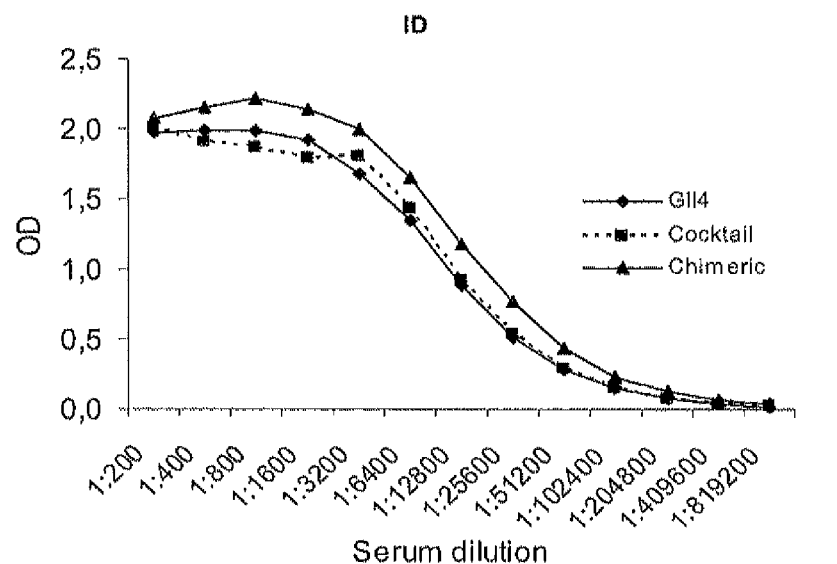
FIG. 6 shows the ELISA results of an IgG end point titration assay of sera from experimental groups of mice immunized intradermally (the upper panel) or intramuscularly (the lower panel) either with GII-4 VLPs alone or in the cocktail or the chimeric formulation with rVP6.
Figure 6:
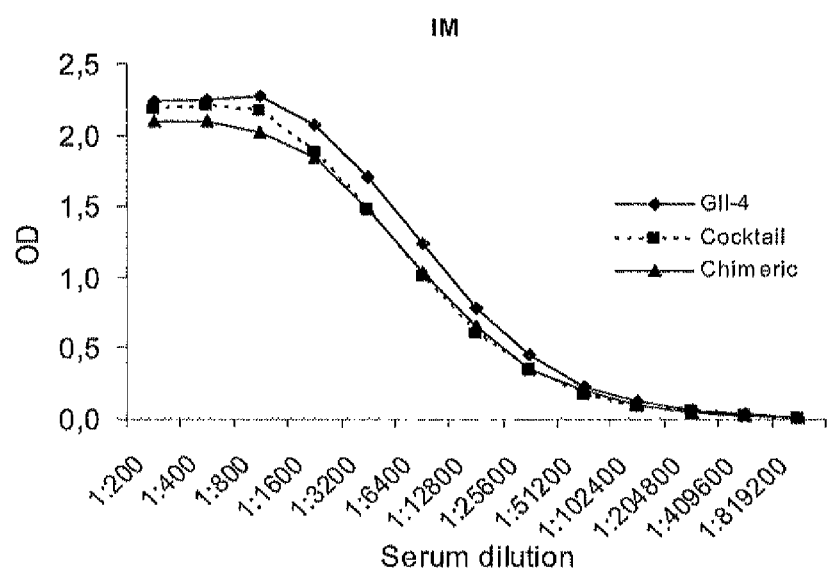
Figure 7:
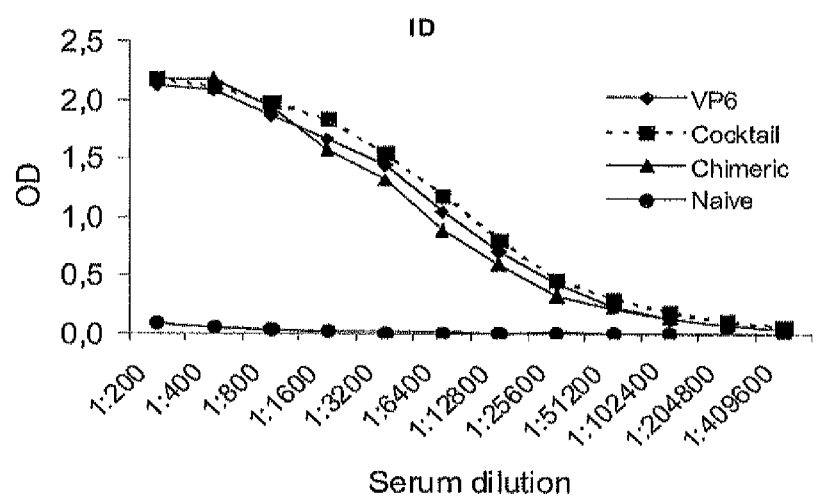
FIG. 7 illustrates the ELISA results of an IgG end point titration assay of sera from experimental groups of mice immunized intradermally (the upper panel) or intramuscularly (the lower panel) either with rVP6 alone or in the cocktail or chimeric formulation with GII-4 VLPs.
Figure 7:
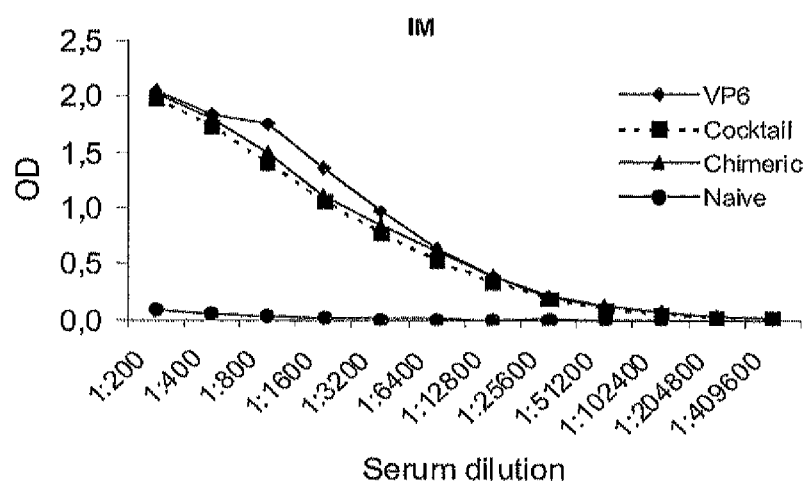

FIGS. 6 and 7 show respective norovirus and rotavirus specific serum IgG titrations. End point titers were appreciably high (reciprocal titer >4 to 5 log10) for each group of the immunized mice except the control mice. These results show that there is no mutual inhibition or suppression of the specific immune responses by the components in the combination vaccine.

Figure 9:
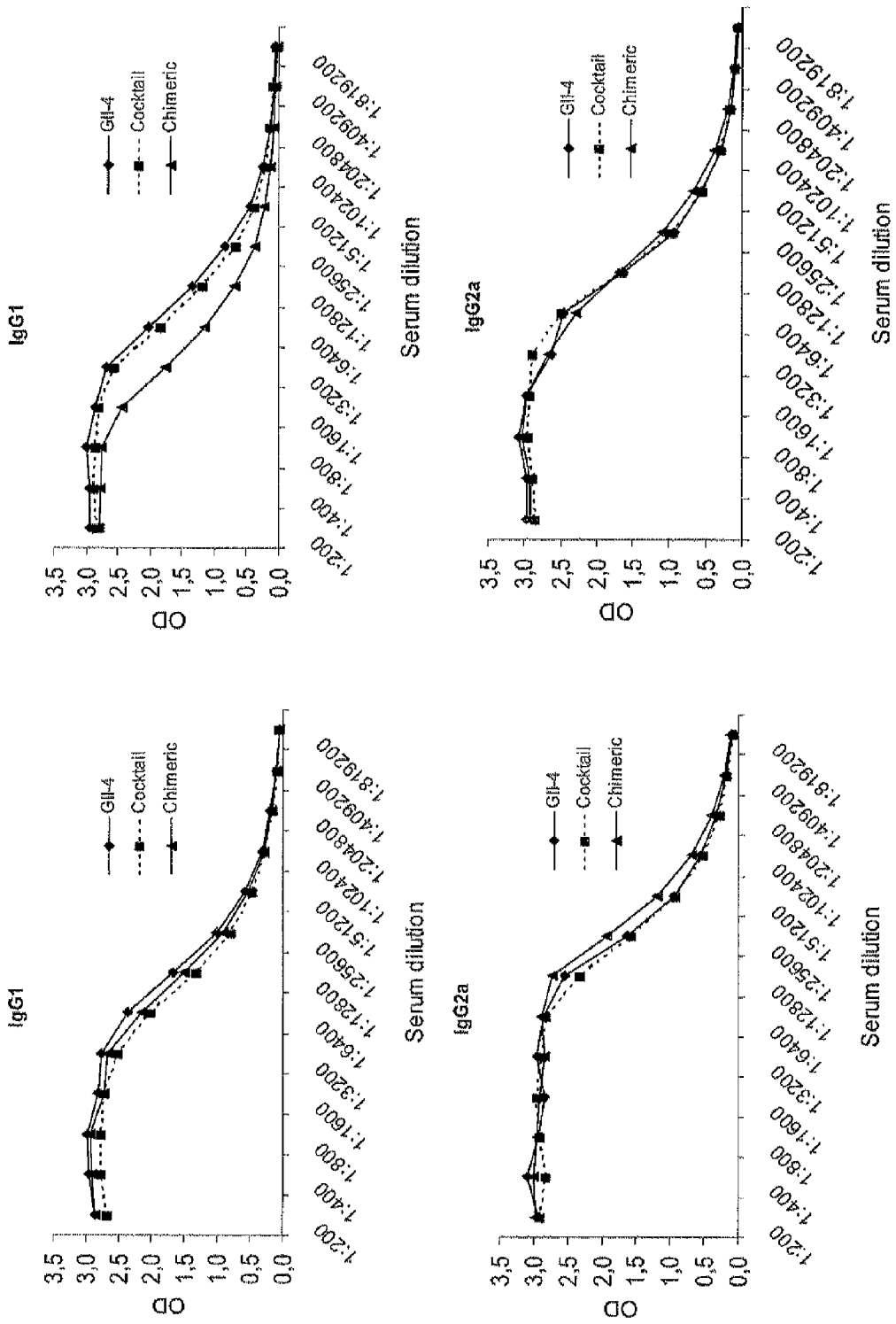
FIG. 9 depicts an end point titration assay of NV-specific IgG1 and IgG2a subtype antibody responses of mice immunized ID (panels to the left) or IM (panels to the right) with GII-4 VLPs alone, the cocktail, or the chimeric formulation.
Figure 10:
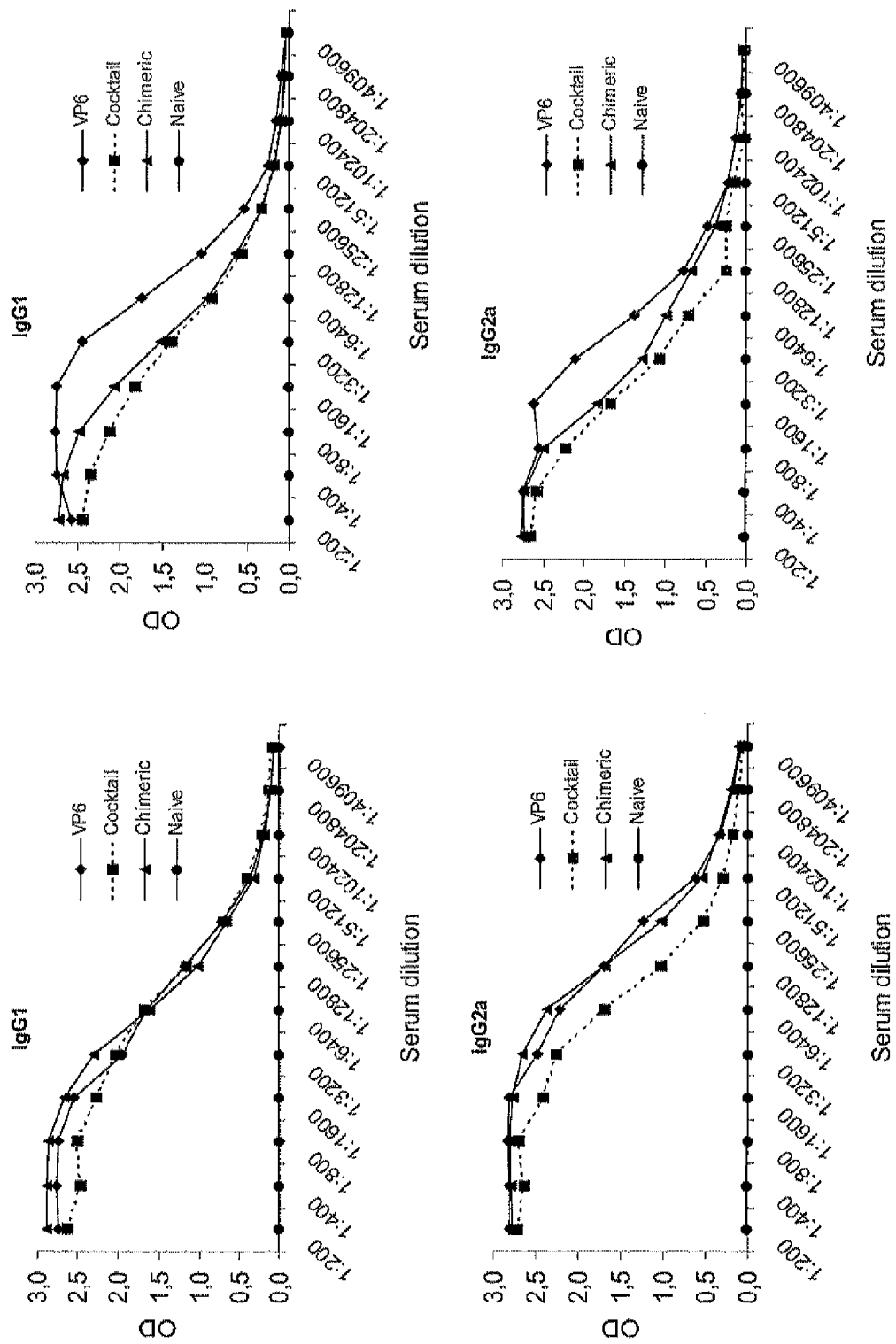
FIG. 10 shows an end point titration assay of RV-specific IgG1 and IgG2a subtype antibody responses of mice immunized ID (panels to the left) or IM (panels to the right) with the rVP6, the cocktail, or the chimeric formulation.

FIGS. 9 and 10 show that all the vaccine formulations of the present invention induce a mixed balanced type of the immune response, namely Th1 type and Th2 type. This is an important observation considering that both types of the immune response are likely to mediate protection against infection with NV and/or RV. Th cells provide help to B cells (either by cell-to-cell contact or soluble cytokines), especially differentiation into memory B cells which are required for the long term memory response aimed to be induced by the vaccines in general. RV VP6-specific Th cells induce protection against murine rotavirus infection and provide cognate help to B cells specific for neutralizing epitopes on the heterotypic VP4 or VP7 molecules of RV (Esquivel F R, Arch. Virology 2000; Peralta et al., Virology Journal, 2009). Therefore, Th cells are important for heterotypic immune response induction.

Example 9

Avidity of Immune Response

Antibody avidity is a measure of functional antibody maturation or affinity maturation. High avidity antibodies have been shown to significantly correlate with the protective efficacy of vaccines (Makidon et al., 2008). We have previously shown (Nurminen et al., 2010) that older children with high avidity NV-specific IgG antibodies in their blood had fewer NV infections than children less than two years of age who had low avidity antibodies.

To determine the avidity of NV and RV antibodies, urea elution was used to remove the low avidity antibodies [Kanno and Kazuyama, 2002]. The ELISA assay was carried out as described above, except for an additional urea incubation step. After incubation of sera on antigen (norovirus GII-4 VLP or rotavirus VP6 protein) coated plates, the sera were aspirated from the plate and 8 M urea (Sigma-Aldrich) in PBS-T was added. After 5 minutes of incubation the treatment was repeated. Plates were washed 4 times prior to the addition of HRP-conjugated anti-mouse IgG and developing the plates as described above. The avidity index was calculated as [OD with urea/OD without urea]×100%, an index value >50% was considered as high avidity.

Figure 11:
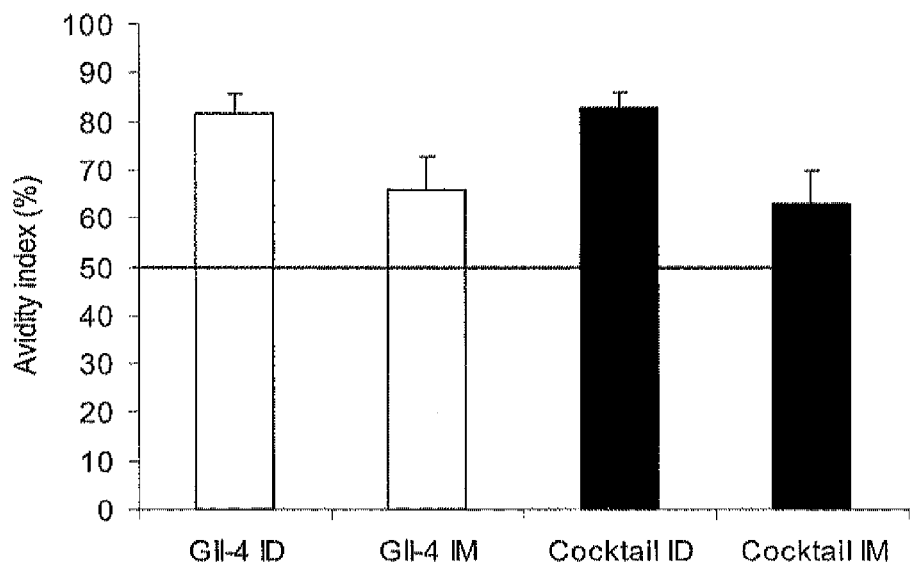
FIG. 11 illustrates the mean avidity indexes (%) of GII-4 (the upper panel) or rVP6 (the lower panel) specific IgG antibodies following the immunizations alone or in the cocktail or the chimeric vaccine formulation. An avidity index 50% is considered as high avidity.
Figure 11:
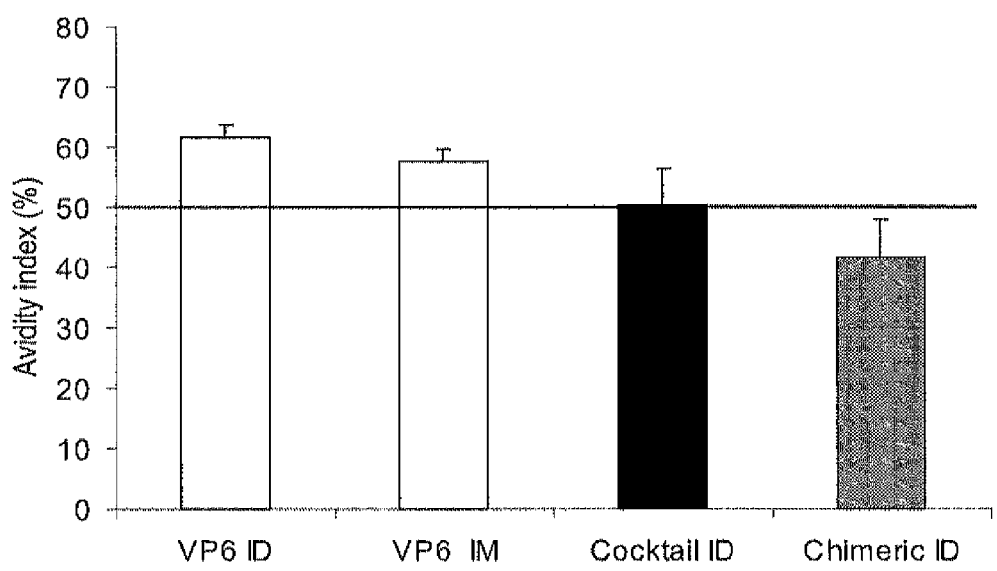

Immunization with the single or the combination vaccine induced NV- and RV-specific IgG antibodies with high avidity (avidity index >50%, respectively). The results show that the present vaccine formulations are potent inducers of the high avidity antibodies with the protective features (FIG. 11).

Example 10

Cross-Reactive Immune Responses

Rotaviruses of different serotypes (G1P8, G2P6, G4P6, G8P10, G12P4, BRV and RRV) were cultured in foetal rhesus monkey kidney (MA104) cells (MA104) and prepared for use as antigens in ELISA for cross-reactivity studies.

Sera from immunized and control mice were tested for norovirus and rotavirus antibodies in ELISA as described in Example 8. Norovirus GII-4-induced serum antibodies were cross-reactive towards heterologous GI-3 and GII-12 antigens (FIG. 12, the upper panel). Moreover, rotavirus-specific serum antibodies of mice immunized with the vaccine formulations were cross-reactive towards different human, bovine and simian rotavirus strains belonging to the subgroups 1 and 2 (FIG. 12, the lower panel).

Surprisingly, a rotavirus VP6 antigen resulted in an approximately 50% increase in the cross-reactive immune response towards GI-3 in the sera of mice immunized with the combination vaccine compared to a rotavirus VP6 single vaccine (FIG. 12, the upper panel). This result shows that the antigenic components of the present combination vaccines provide a synergistic effect.

Example 11

Blocking Assay

Blocking assay is a surrogate neutralization assay for NV. NV cannot be grown in cell cultures in vitro, and therefore a neutralization assay in classical terms with antibodies blocking the virus to bind and infect permissive cells is impossible to perform. Human histo-blood group antigens (HBGA) have recently been discovered as receptors for NV expressed on the cells of mucosal surfaces (e.g. enterocytes) among others. For example, a carbohydrate H type 3 has been identified as a putative receptor for NV GII-4 and therefore GII-4 VLPs bind to the above carbohydrate (L Huhti et al., 2010). The binding of NV VLPs to the receptor is expected to be blocked with the antibodies with neutralization properties. Indeed, binding of GII-4 VLPs to H-type 3 could be blocked by sera from children not infected with NV during a waterborne outbreak of acute gastroenteritis (K Nurminen et al., 2010). Protection against NV infection correlated with strong blocking activity of the sera. Therefore, blocking activity of the antibodies may be a relevant surrogate marker of NV protection when considering different vaccine approaches.

The assay for blocking the binding of NV VLPs to HBGA H-type 3 was performed with immunized and control mice sera. Microtiter plates were coated with GII-4 or GI-3 VLPs in PBS (pH 7.2) at a concentration of 2 µg/ml and incubated 4 h at RT. After washing, the plates were incubated with 5% milk in PBS overnight at 4° C. Sera serially diluted from 1:200 to 1:6400 were added to the wells and the plates were incubated 1 h at 37° C. After aspirating the sera 100 µl of biotinylated H-type-3 or Lewis B (Leu$^b$) (Lectinity Holdings, Inc., Moscow, Russia) as a control was added at a concentration of 20 µg/ml or 40 µg/ml in PBS-T containing 1% milk. After 4 h at 37° C. the wells were washed and a 1:2000 dilution of streptavidin-conjugated HRP (Thermo Fisher Scientific Inc.) was added and incubated 1 h at 37° C. The development of the colour reaction and the measurement of absorbance at a wavelength of 490 nm were conducted as described above. OD reading from the wells incubated without serum was considered as a maximum signal for the binding of H-type 3 to GII-4 VLP. The blocking index was calculated as follows: 100%—(OD[with serum]/OD[without serum]×100%). No binding of VLPs to the negative control Leu$^b$ HBGA was detected. A background signal from the blank wells (wells lacking HBGA) was subtracted from all of the OD values of tested samples.

FIGS. 13A and 13B show blocking of the GII-4 and GI-3 binding to their putative receptor H type 3, respectively. A two-fold greater titer was needed to maximally block the binding of GII-4 VLPs to the H type 3 of mice immunized with a single vaccine compared to the combined vaccine (FIG. 13C). This result shows that the rVP6 protein in the combination vaccine is not suppressing or inhibiting the blocking activity of the GII-4 specific sera. On the contrary, the remarkable blocking activity of the sera of mice immunized by the combination vaccine formulation indicates an adjuvant effect of the rVP6 protein similar to the one detected in the previous experiment. Moreover, our data show that cross-protection between genogroups is readily detectable with the vaccine formulations used in our study. This kind of observation is quite unique in a field of norovirus vaccine research. The results also show that immunization with one strain/genotype of the virus (a so-called monovalent vaccine) will not only induce a cross-reactive or heterotypic immune response against other strains not included in the vaccine formulations as described above but it will also block heterologous virus binding and neutralize it.

Example 12

Antibody Secreting Cells (ASC) ELISPOT

Antibody secreting cells (ASC) are divided into plasma B cells and memory B cells which are responsible for long-term protection against a pathogen (a memory response) and will react quickly to the pathogen upon re-exposure which is a hallmark of the memory response aimed to be induced by any vaccination. An ELISPOT assay was used to detect the frequency of IgG antibody secreting plasma cells and memory B cells in the spleen of immunized mice.

Spleens from euthanized mice were collected in Hanks balanced salt solution (HBSS) (Sigma-Aldrich). The structure of the spleen was disrupted with a scalpel and dissociated into single cell suspension by using 70 µm cell strainers (Becton, Dickinson and Company, USA). The suspensions were centrifuged 300×g for 10 minutes and the cells resuspended in HBSS. Red blood cells were lysed with 1:10 diluted HBSS, after which the molarity of the suspension was recovered with 2×HBSS. Splenocyte suspensions were washed three times, frozen in freezing media (RPMI supplemented with 40% FBS and 10% DMSO, Sigma-Aldrich), and stored in liquid nitrogen for further use.

96-well PVDF plates (Millipore) were coated overnight at +4° C. with norovirus GII-4 VLPs or rotavirus VP6 proteins at a concentration of 40 µg/ml in a volume of 100 µl/well. Splenocytes were thawed from liquid nitrogen, washed and suspended in cell culture media (RPMI-1640 supplemented with 10% FBS, 100 U/ml penicillin, 100 µg/ml streptomycin, 50 µM 2-mercaptoethanol and 2 mM L-glutamine). After washing and blocking the plate, splenocytes were added at a concentration of 4×10$^5$ cells/well and incubated overnight at +37° C., 5% CO$_2$. The plates were washed 6 times with PBS-T, and goat anti-mouse IgG-HRP (Sigma-Aldrich) was added to the wells at the dilution of 1:1000. After 3 hours of incubation at RT, the plates were intensively washed and developed with a DAB substrate (SigmaFAST DAB, Sigma-Aldrich), and the spots were counted. Spots appearing in wells from naïve control animals were subtracted from the experimental group. The data is expressed as GII-4 VLP or VP6 specific antibody-secreting cells (ACS) and is normalized per 1×10$^6$ cells.

In some instances, the cells were incubated in vitro for four days with the GII-4 VLPs or the rVP6, washed and plated as described in connection with memory B cells quantification. The spots obtained from the ELISPOT assay performed with the cells without in vitro stimulation were assumed to be actively-secreting plasma cells. The spots obtained with the 4-day cultured cells, after subtracting plasma cell-generated spots, represent memory B cell activity.

FIG. 14 shows that the present vaccine formulations induce plasma B cells producing NV and RV specific IgG antibodies. Also, high frequencies of memory B cells secreting specific IgG antibodies are induced at similar quantities with the single and combination vaccines showing that the response induced is a memory one.

References

Buesa J, Collado B, Lopez-Andújar P, Abu-Mallouh R, Rodriguez Diaz J, Garcia Diaz A, Prat J, Guix 5, Llovet T, Prats G, Bosch A. Molecular epidemiology of caliciviruses causing outbreaks and sporadic cases of acute gastroenteritis in Spain. J Clin Microbiol. 2002 August; 40(8):2854-9.

Burns J W, Siadat-Pajouh M, Krishnaney A A, Greenberg H B. Protective effect of rotavirus VP6-specific IgA monoclonal antibodies that lack neutralizing activity. Science. 1996 Apr. 5; 272(5258):104-7.

Esquivel F R, Lopez S, Guitierrez-X L, Arias C. The internal rotavirus protein VP6 primes for an enhanced neutralizing antibody response. Arch Virol. 2000;145(4):813-25.

Estes M K, Crawford S E, Penaranda M E, Petrie B L, Burns J W, Chan W K, Ericson B, Smith G E, Summers M D. Synthesis and immunogenicity of the rotavirus major capsid antigen using a baculovirus expression system. J Virol. 1987 May: 81(5): 1488-94.

Fifis T, Gamvrellis A, Crimeen-Irwin B, Pietersz G A, Li J, Mottram P L, McKenzie I F, Plebanski M. Size-dependent immunogenicity: therapeutic and protective properties of nano-vaccines against tumors. J Immunol. 2004 Sep. 1; 173 (5):3148-54.

Huhti L, Blazevic V, Nurminen K, Koho T, Hytönen V P, Vesikari T. A comparison of methods for purification and concentration of norovirus GII-4 capsid virus-like particles. Arch Virol. 2010 Aug. 19. [Epub ahead of print]

Jiang X, Wang M, Graham D Y, Estes M K. Expression, self-assembly, and antigenicity of the Norwalk virus capsid protein. J Virol. 1992 November; 66(11):6527-32.

Kanno A, Kazuyama Y. Immunoglobulin G antibody avidity assay for serodiagnosis of hepatitis C virus infection. J Med Virol. 2002 October; 68(2):229-33.

Keller S A, Bauer M, Manolova V, Muntwiler S, Saudan P, Bachmann M F. Cutting edge: limited specialization of dendritic cell subsets for MHC class II-associated presentation of viral particles. J Immunol. 2010 Jan. 1; 184(1):26-9. Epub 2009 Nov. 30.

Lepault J, Petitpas I, Erk I, Navaza J, Bigot D, Dona M, Vachette P, Cohen J, Rey F A. Structural polymorphism of the major capsid protein of rotavirus. EMBO J. 2001 Apr. 2; 20(7):1498-507.

Makidon P E, Bielinska A U, Nigavekar S S, Janczak K W, Knowlton J, Scott A J, Mank N, Cao Z, Rathinavelu S, Beer M R, Wilkinson J E, Blanco L P, Landers J J, Baker J R Jr. Pre-clinical evaluation of a novel nanoemulsion-based hepatitis B mucosal vaccine. PLoS One. 2008 Aug. 13; 3(8): e2954.

Matthijnssens J, Rahman M, Martella V, Xuelei Y, De Vos S, De Leener K, Ciarlet M, Buonavoglia C, Van Ranst M. Full genomic analysis of human rotavirus strain B4106 and lapine rotavirus strain 30/96 provides evidence for interspecies transmission. J Virol. 2006 April; 80(8):3801-10.

Nurminen K, Blazevic V, Huhti L, Koho T, Hytönen V P, Vesikari T. Prevalence of norovirus GII-4 antibodies in Finnish children. J Med Virol (accepted for publication).

Parez N, Garbarg-Chenon A, Fourgeux C, Le Deist F, Servant-Delmas A, Charpilienne A, Cohen J, Schwartz-Cornil I. The VP6 protein of rotavirus interacts with a large fraction of human naive B cells via surface immunoglobulins. J Virol. 2004 November; 78(22):12489-96.

Peralta A, Molinari P, Taboga O. Chimeric recombinant rotavirus-like particles as a vehicle for the display of heterologous epitopes. Virol J. 2009 Nov. 6; 6:192.

Vesikari T, Karvonen A, Prymula R, Schuster V, Tejedor J C, Cohen R, Meurice F, Han H H, Damaso S, Bouckenooghe A. Efficacy of human rotavirus vaccine against rotavirus gastroenteritis during the first 2 years of life in European infants: randomised, double-blind controlled study. Lancet. 2007 Nov. 24; 370(9601):1757-63.

Vesikari T, Matson D O, Dennehy P, Van Damme P, Santosham M, Rodriguez Z, Dallas M J, Heyse J F, Goveia M G, Black S B, Shinefield H R, Christie C D, Ylitalo S, Itzler R F, Coia M L, Onorato M T, Adeyi B A, Marshall G S, Gothefors L, Campens D, Karvonen A, Watt J P, O'Brien K L, DiNubile M J, Clark H F, Boslego J W, Offit P A, Heaton P M; Rotavirus Efficacy and Safety Trial (REST) Study Team. Safety and efficacy of a pentavalent human-bovine (WC3) reassortant rotavirus vaccine. N Engl J Med. 2006 Jan. 5; 354(1):23-33.

The invention claimed is:

1. An immunogenic composition comprising at least one norovirus VLP comprising a norovirus GII-4 VLP, and at least one rotavirus VP6 antigen.

2. The immunogenic composition according to claim 1, further comprising a norovirus antigen selected from the group consisting of antigenic capsid peptides, and antigenic capsid proteins.

3. The immunogenic composition according to claim 1, wherein said GII-4 VLP is monovalent.

4. The immunogenic composition according to claim 1, wherein more than one type of norovirus VLP is present in the immunogenic composition.

5. The immunogenic composition according to claim 1, wherein said rotavirus VP6 antigen is selected from the group consisting of recombinant VP6 (rVP6) protein, double-layered VP2/VP6 VLP, VLPs comprising VP6 protein, and any combinations thereof.

6. The immunogenic composition according to claim 5, wherein said rVP6 protein is in a multimeric form selected from the group consisting of tubules, spheres, sheets, and any combinations thereof.

7. The immunogenic composition according to claim 1, further comprising a sterile, nontoxic pharmaceutically acceptable physiological carrier.

8. The immunogenic composition according to claim 1, wherein the immunogenic composition is capable of inducing an immune response that inhibits at least one member selected from the group consisting of: norovirus and rotavirus infections, norovirus and rotavirus induced diarrheal and vomiting diseases, and norovirus and rotavirus induced gastroenteritis.

9. A method comprising administering the immunogenic composition according to claim 1, to a subject in need thereof to induce an immune response to inhibit at least one member selected from the group consisting of: norovirus and rotavirus infections, norovirus and rotavirus induced diarrheal and vomiting diseases, and norovirus and rotavirus induced gastroenteritis.

10. A method of producing the immunogenic composition according to claim 1, comprising
 a) co-expressing at least one norovirus GII-4 VLP and at least one rotavirus VP6 protein in a cell culture, and
 b) isolation the VLP and VP6 proteins from the cell culture.

11. The method according to claim 10, wherein said norovirus and rotavirus proteins are produced in recombinant baculovirus-infected insect cells.

12. A method of producing the immunogenic composition according to claim 1, comprising the steps of:
 a) producing a norovirus GII-4 VLP in cell culture, isolating the VLP, and purifying the VLP;
 b) producing a rotavirus VP6 protein in cell culture, isolating the VP6 protein, and purifying a rotavirus VP6 protein; and
 c) mixing said norovirus VLP and rotavirus VP6 proteins.

13. The method according to claim 12, wherein said norovirus and rotavirus proteins are produced in recombinant baculovirus-infected insect cells.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gtgaatgaag atggcgtcga                                              20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ttataatgca cgtctacgcc c                                            21
```

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
cacaggatcc atgaagatgg cgtcgaatga c                          31

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
ctctgaattc ttataatgca cgtctacgcc ccgctcca                   38

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gtgaatgaag atggcgtcga                                       20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ttactgtact cttctgcgcc c                                     21

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gtaaatgatg atggcgtcta a                                     21

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tgggccatta tgatctccta at                                    22